(12) United States Patent
Bird

(10) Patent No.: US 6,251,913 B1
(45) Date of Patent: Jun. 26, 2001

(54) HYDROXAMIC ACIDS SUBSTITUTED BY HETEROCYCLES USEFUL FOR INHIBITION OF TUMOR NECROSIS FACTOR

(75) Inventor: Thomas Geoffrey Colerick Bird, Reims (FR)

(73) Assignees: Zeneca Limited, London (GB); Zeneca Pharma S.A., Cergy Cedex (FR)

( * ) Notice: Subject to any disclaimer, the term of this patent is extended or adjusted under 35 U.S.C. 154(b) by 0 days.

(21) Appl. No.: 09/381,836
(22) PCT Filed: Mar. 25, 1998
(86) PCT No.: PCT/GB98/00910
§ 371 Date: Sep. 24, 1999
§ 102(e) Date: Sep. 24, 1999
(87) PCT Pub. No.: WO98/43959
PCT Pub. Date: Oct. 8, 1998

(30) Foreign Application Priority Data

Mar. 28, 1997 (EP) .................................................. 97400725

(51) Int. Cl.$^7$ ................... A61K 31/4704; A61K 31/505; C07D 215/14; C07D 239/90; C07D 263/64
(52) U.S. Cl. .......................... 514/259; 514/307; 514/311; 544/135; 544/137; 544/283; 544/286; 546/134; 546/139; 546/201; 548/495; 560/312; 562/623
(58) Field of Search .................................. 544/286, 283, 544/135, 137; 514/259, 311, 307; 548/495; 546/134, 139, 201; 560/312; 562/623

(56) References Cited

FOREIGN PATENT DOCUMENTS

| 2 268 933 | 1/1994 | (GB) . |
| 94 10990 | 5/1994 | (WO) . |
| 95 19961 | 7/1995 | (WO) . |
| 96 25156 | 8/1996 | (WO) . |

*Primary Examiner*—Richard L. Raymond
*Assistant Examiner*—Venkataraman Balasubramanian
(74) *Attorney, Agent, or Firm*—Pillsbury Winthrop LLP

(57) ABSTRACT

Compounds of formula (I),

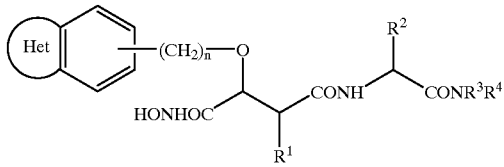

(I)

wherein: n is 1 to 6; Het is a nitrogen containing ring fused to the benzene ring on two adjacent carbon atoms to form a bicyclic ring system which ring system may be optionally substituted; $R^1$ is hydrogen, $C_{1-8}$alkyl, $C_{2-6}$alkenyl, $C_{2-6}$alkyny, $C_{3-8}$cycloalkyl, aryl, heteroaryl, heterocyclyl, aryl$C_{1-6}$alkyl, heteroaryl$C_{1-6}$alkyl, heterocyclyl$C_{1-6}$alkyl or $C_{3-8}$cycloalkyl$C_{1-6}$alkyl; $R^2$ is $C_{1-6}$alkyl, $C_{2-6}$alkenyl, aryl$C_{1-6}$alkyl, heteroaryl$C_{1-6}$alkyl or the side-chain of a naturally occurring amino acid; $R^3$ is hydrogen, $C_{1-6}$alkyl, $C_{3-8}$cycloalkyl, $C_{4-8}$cycloalkenyl, aryl$C_{1-6}$alkyl, heteroaryl$C_{1-6}$alkyl or heterocycyl$C_{1-6}$alkyl; $R^4$ is hydrogen or $C_{1-6}$alkyl; or $R^3$ and $R^4$ together with the nitrogen atom to which they are joined form a heterocyclic ring; wherein any group or ring, in $R^1$–$R^4$, is optionally substituted; and pharmaceutically acceptable salts and in vivo hydrolysable esters thereof, are described as inhibitors of the production of Tumor Necrosis Factor and/or one or more matrix metalloproteinase enzymes. Compositions containing them and their preparation are also described.

9 Claims, No Drawings

HYDROXAMIC ACIDS SUBSTITUTED BY HETEROCYCLES USEFUL FOR INHIBITION OF TUMOR NECROSIS FACTOR

This application is the national phase of international application PCT /GB98/00910 filed Mar. 25, 1998.

This invention relates to hydroxamic acid compounds and in particular to such compounds with a heterocyclicalkoxy substituent. This invention further relates to processes for preparing such compounds, to pharmaceutical compositions containing them and to their use in methods of therapeutic treatment.

The compounds of this invention are inhibitors of the production of TNF (Tumour Necrosis Factor) which is believed to be formed by the cleavage of a pro-form, or larger precursor, by the enzyme pro-TNF Convertase. Applicants believe that the compounds of the present invention inhibit TNF production by mechanisms which include inhibition of pro-TNF Convertase. The term 'TNF' is used herein to refer to Tumour Necrosis Factor in general but, in particular to TNFα.

The compounds of this invention will be useful in the treatment of disease or medical conditions in which excessive TNF production is known to give rise via a cascade of processes to a variety of physiological sequelae including the production of physiologically-active eicosanoids such as the prostaglandins and leukotrienes, the stimulation of the release of proteolytic enzymes such as collagenase, the activation of osteoclast activity leading to the resorption of calcium, the stimulation of the release of proteoglycans from, for example, cartilage, the stimulation of cell proliferations and to angiogenesis. It is also known that, in certain cellular systems, TNF production precedes and mediates the production of other cytokines such as interleukin-1 (IL-1) and interleukin-2 (IL-2) which are also believed to contribute to the pathology of disease states such as inflammatory and allergic diseases and cytokine-induced toxicity. Excessive TNF production has also been implicated in mediating or exacerbating the development of various inflammatory and allergic diseases such as inflammation of the joints (especially rheumatoid arthritis, osteoarthritis and gout), inflammation of the gastrointestinal tract inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular disorders such as myocardial infarction, angina and peripheral vascular disease. Excessive TNF production has also been implicated in mediating complications of bacterial, fungal and/or viral infections such as endotoxic shock, septic shock and toxic shock syndrome. Excessive TNF production has also been implicated in mediating or exacerbating the development of adult respiratory distress syndrome, diseases involving cartilage or muscle resorption, Paget's disease and osteoporosis, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

The compounds of the invention may also be inhibitors of one or more matrix metalloproteinases such as collagenases, stromelysins and gelatinases. Thus they may also be of use in the therapeutic treatment of disease conditions mediated by such enzymes for example arthritis (rheumatoid and osteoarthritis), osteoporosis and tumour metastasis.

The present invention provides novel compounds which have activity as inhibitors of TNF and/or are inhibitors of one or more matrix metalloproteinase enzymes.

Accordingly the present invention provides a compound of the formula (I):

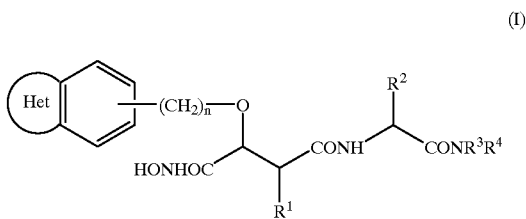

(I)

wherein:

n is 1 to 6;

Het is a nitrogen containing ring fused to the benzene ring on two adjacent carbon atoms to form a bicyclic ring system which ring system may be optionally substituted;

$R^1$ is is hydrogen, $C_{1-8}$alkyl, $C_{2-6}$alkenyl, $C_{2-6}$alkynyl, $C_{3-8}$cycloalkyl, aryl, heteroaryl, heterocyclyl, aryl$C_{1-6}$alkyl, heteroaryl$C_{1-6}$alkyl, heterocyclyl$C_{1-6}$alkyl or $C_{3-8}$cycloalkyl$C_{1-6}$alkyl;

$R^2$ is $C_{1-6}$alkyl, $C_{2-6}$alkenyl, aryl$C_{1-6}$alkyl, heteroaryl$C_{1-6}$alkyl or the side-chain of a naturally occurring amino acid;

$R^3$ is hydrogen, $C_{1-6}$alkyl, $C_{3-8}$cycloalkyl, $C_{4-8}$cycloalkenyl, aryl$C_{1-6}$alkyl, heteroaryl$C_{1-6}$alkyl or heterocyclyl$C_{1-6}$alkyl;

$R^4$ is hydrogen or $C_{1-6}$alkyl; or $R^3$ or $R^4$ together with the nitrogen atom to which they are joined form a heterocyclic ring;

wherein any group or ring, in $R^1$–$R^4$, is optionally substituted;

or a pharmaceutically acceptable salt or in vivo hydrolysable ester thereof.

"Aryl in the terms "aryl " and "aryl $C_{1-6}$alkyl" typically means phenyl or naphthyl, preferably phenyl, "Heteroaryl" in the terms "heteroaryl" and "heteroaryl$C_{1-6}$alkyl" means an aromatic mono- or bicyclic 5–10 membered ring with up to five ring heteroatoms selected from nitrogen, oxygen and sulphur. Examples of 'heteroaryl ' include thienyl, pyrrolyl, furanyl, imidazolyl, thiazolyl, pyrimidinyl, pyridinyl, indolyl, benzimidazolyl, benzthiazolyl, quinolinyl and isoquinolinyl. "Heterocyclyl" in the terms "heterocyclyl" and heterocyclyl-$C_{1-6}$alkyl" means a non-aromatic mono- or bicyclic 5–10 membered ring with up to five ring hetero atoms selected from nitrogen, oxygen and sulphur. Examples of 'heterocyclyl' include pyrrolidinyl, morpholinyl, piperidinyl, dihydropyridinyl and dihydropyrimidinyl.

Any group or ring in $R^1$–$R^4$ may be optionally substituted, for example by up to three substituents which may be the same or different. Typical substituents include: hydroxy, $C_{1-6}$alkoxy for example methoxy, mercapto, $C_{1-6}$alkylthio for example methylthio, amino, $C_{1-6}$alkylamino for example methylamino, di-($C_{1-6}$alkyl)amino for example dimethylamino, carboxy, carbamoyl, $C_{1-6}$alkylcarbamoyl for example methylcarbamoyl, di-$C_{1-6}$alkylcarbamoyl for example dimethylcarbamoyl, $C_{1-6}$alkylsulphonyl for example methylsulphonyl, arylsulphonyl for example phenylsulphonyl, $C_{1-6}$alkylaminosulphonyl for example methylaminosulphonyl, di-($C_{1-6}$alkyl)aminosulphonyl for example dimethylamino-sulphonyl, nitro, cyano, cyano$C_{1-6}$alkyl for example cyanomethyl, hydroxy$C_{1-6}$alkyl for example hydroxymethyl, amino $C_{1-6}$alkyl for example aminoethyl, $C_{1-6}$alkanoylamino for example acetamido, $C_{1-6}$alkoxycarbonylamino for example methoxycarbonylamino, $C_{1-6}$Alkanoyl for example acetyl, $C_{1-6}$alkanoyloxy for example acetoxy, $C_{1-6}$alkyl for example methyl, ethyl, isopropyl or tert-butyl, halo for example fluoro, chloro or bromo, trifluoromethyl, aryl for example phenyl, aryl$C_{1-6}$alkyl for example benzyl, aryloxy for example phenoxy, aryl$C_{1-6}$alkoxy for example benzyloxy, heteroaryl, heteroaryl$C_{1-6}$alkyl, heterocyclyl and heterocyclyl$C_{1-6}$alkyl, The term "side chain of a naturally occurring amino acid" means the side chain X of an amino acid $NH_2$—CHX—COOH. Suitable amino acids include alanine, arginine, aspartic acid, cysteine, asparagine, glutamine, histidine, homoserine, isoleucine, leucine, lysine, methionine, norleucine, norvaline, ornithine, serine, theonine, tryptophan, tyrosine and valine.

The compounds of the present invention possess a number of chiral centres, at the carbon atom adjacent to the HONHOC— group, at —CHR$^2$—, at —CHR$^1$—(when R$^1$ is not hydrogen) and possibly in the variables R$^1$–R$^4$. The present invention covers all diastereoisomers and mixtures thereof that inhibit TNF Convertase and/or inhibit matrix metalloproteinase enzymes.

n is 1 to 6, preferably n is 1 or 2 forming a methylene or ethylene moiety. Most preferably n is 1 forming a methylene moiety.

Suitably Het is a ring containing one or two ring nitrogen atoms. Suitably Het, together with the two fused carbon atoms, is a 5- or 6-membered ring. Therefore in a particular aspect Het is a 5- or 6-membered ring containing one or two ring nitrogen atoms.

In one aspect Het and the benzene ring to which it is fused form a bicyclic heteroaryl ring system for example quinoline, quinazoline, phthalazine, cinnoline, isoquinoline, indole, isoindole or indazole. In a further aspect Het and the benzene ring to which it is fused form quinoxaline.

Preferably benzene-Het is quinoline, quinazoline or isoquinoline.

In another aspect Het is a pyridone or pyrimidone ring such as of the sub-formulae (i)–(iii):

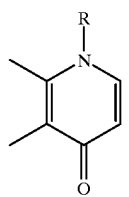
(i)

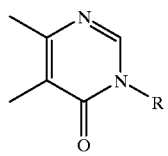
(ii)

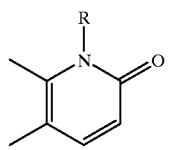
(iii)

wherein R is hydrogen or $C_{1-6}$alkyl [Compounds wherein R is hydrogen may be regarded as keto-tautomers of the corresponding aromatic system substituted by hydroxy].

Preferably Het is a pyridone or pyrimidone ring of the sub-formula (ii) or (iii).

In another further aspect Het is a tetrahydropyridone or tetrahydropyrimidone ring forming for example a bicyclic tetrahydroquinolone system. Het may also be an oxazine forming a benzoxazine ring system.

In yet a further aspect Het is a five-membered ring for example an oxazole, thiazole, pyrrole or dihydropyrrole forming for example a benzoxazole, benzthiazole, indole or dihydroindole ring system.

The bicyclic ring system formed by Het and the benzene ring may be optionally substituted, or either ring, by up to three substituents which may be the same or different. Typical substituents include those described hereinbefore in relation to any group or ring in R$^1$–R$^4$. In particular, preferred substituents for the benzene-Het fused bicyclic ring system are $C_{1-6}$alkyl, halo, hydroxy, amino, $C_{1-6}$alkylamino and di-$C_{1-6}$alkylamino.

The —O(CH$_2$)$_n$— moiety may be linked to any convenient carbon atom of the benzene ring.

Particularly preferred values for the bicyclic ring system are quinoline, isoquinoline, quinazoline, 1-methyl-2-oxo-1,2-dihydroquinoline, 2-methyl-4-hydroxyquinazoline and 2-methyl-4hydroxy-7-bromoquinazoline. Further preferred values for the bicyclic ring system are benzoxazole and 2-methylbenzothiazole.

Particular groups for R$^2$ include $C_{1-8}$alkyl for example isopropyl, n-propyl, isobutyl, sec-butyl, n-butyl, tert-butyl, isopentyl, n-pentyl, hexyl, heptyl or octyl; $C_{1-8}$alkyl interrupted by an oxygen or sulphur atom for example methoxypropyl, ethoxyethyl, propoxymethyl, ethylthioethyl or methylthiopropyl; phenyl$C_{1-6}$alkyl for example benzyl, phenethyl, phenylpropyl or phenylbutyl; aryl$C_{1-6}$alkyl interrupted by oxygen or sulphur for example benzyloxybutyl or benzyloxypropyl; $C_{3-8}$cycloalkyl for example cyclopropyl, cyclobutyl, cyclopentyl or cyclohexyl; or $C_{3-8}$cycloalkyl$C_{1-6}$alkyl for example cyclopropylmethyl, cyclopropylethyl, cyclobutylmethyl, cyclopentylmethyl or cyclohexylmethyl.

Preferably R$^1$ is isobutyl.

There is a chiral centre at —CHR$^1$—(when R$^1$ is not hydrogen); it is preferred that this centre has the configuration indicated in formula (II) hereinafter. For most values of R$^1$ this centre will have the R-stereochemistry under the Cahn-Prelog-Ingold sequence rules.

Particular groups for R$^2$ include $C_{1-6}$alkyl for example methyl, ethyl, isopropyl, n-propyl, n-butyl, isobutyl, sec-butyl, tert-butyl, isopentyl, n-pentyl or hexyl; $C_{1-6}$alkyl interrupted by an oxygen or sulphur atom for example methoxyethyl, methoxypropyl, methylthioethyl or 1.1-dimethylmethylthiomethyl (MeSCMe$_2$—); or phenyl$C_{1-6}$alkyl for example benzyl or phenethyl.

Preferably R$^2$ is isobutyl, tert-butyl, 1,1-dimethylmethylthiomethyl or benzyl with tert-butyl being most preferred.

The chiral centre at —CHR$^2$— preferably has the configuration indicated in formula (II) hereinafter. For most of R$^2$ this centre will have the S-stereochemistry.

Particular groups for R$^3$ include $C_{1-6}$alkyl for example methyl, ethyl, n-propyl, isopropyl, tert-butyl or n-butyl; $C_{1-6}$alkyl interrupted by an oxygen or sulphur atom for example hydroxyethyl, methoxyethyl, methylthioethyl or ethoxyethyl; $C_{2-6}$alkyl substituted by either amino, $C_{1-6}$alkylamino or di-$C_{1-6}$alkylamino; phenyl$C_{1-6}$alkyl for example benzyl, phenethyl or phenylpropyl; heterocyclicalkyl for example 2-morpholinoethyl, 2-piperazinoethyl, 2-(N-methylpiperazino)ethyl or 2-piperidinoethyl; or $C_{3-8}$cycloalkyl$C_{1-6}$alkyl for example cyclopropylmethyl, cyclobutylmethyl or cyclopentylmethyl.

Preferably $R^3$ is methyl, ethyl, n-propyl, isobutyl, tert-butyl or benzyl. Of these methyl is most preferred.

Particular groups for $R^4$ are hydrogen and $C_{1-6}$alkyl for example methyl or ethyl. Preferably $R^4$ is hydrogen.

A particularly suitable class of compounds of the present invention is that of formula (II):

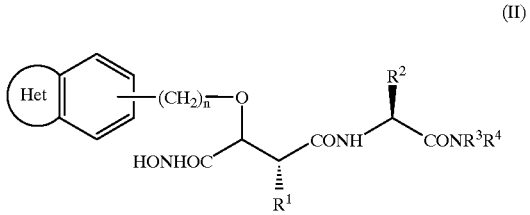

(II)

wherein n, Het, $R^1, R^2, R^3$ and $R^4$ are as hereinbefore defined.

A preferred class of compounds of the formula (II) is that wherein n Is 1; Het and the benzene ring to which it is fused is quinoline, quinazoline, or isoquinoline, any of which is unsubstituted or substituted by one or two groups selected from halogen for example chloro, bromo or fluoro, $C_{1-6}$alkyl for example methyl, isopropyl or tert-butyl, $C_{1-6}$alkoxy for example methoxy, hydroxy, amino, $C_{1-6}$alkylamino for example methylamino or di-$C_{1-6}$alkylamino for example dimethylamino; $R^1$ is isobutyl; $R^2$ is isobutyl, tert-butyl or benzyl; $R^3$ is methyl, ethyl, n-propyl, isobutyl, tert-butyl, 2-dimethylaminoethyl or benzyl; and $R^4$ is hydrogen or methyl.

A further preferred class of compounds of the formula (II) is that wherein n is 1; Het is of the sub-formula (ii) or (iii) wherein either of such rings is unsubstituted or substituted by one or two groups selected from halogen for example chloro, bromo or fluoro, $C_{1-6}$alkyl for example methyl, isopropyl or tert-butyl, $C_{1-6}$alkoxy for example methoxy, hydroxy, amino, $C_{1-6}$alkylamino for example methylamino or di-$C_{1-6}$alkylamino for example dimethylamino; $R^1$ is isobutyl; $R^2$ is isobutyl, tert-butyl or benzyl; $R^3$ is methyl, ethyl, n-propyl, isobutyl, tert-butyl, 2-dimethylaminoethyl or benzyl; and $R^4$ is hydrogen or methyl.

Suitable pharmaceutically acceptable salts include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

In vivo hydrolysable esters are those pharmaceutically acceptable esters that hydrolyse in the human body to produce the parent compound. Such esters can be identified by administering, for example intravenously to a test animal, the compound under test and subsequently examining the test animal's body fluids. Suitable in vivo hydrolysable esters for carboxy include methoxymethyl and for hydroxy include acetyl.

In order to use a compound of the formula (I) or a pharmaceutically acceptable salt or in vivo hydrolysable ester thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or an in vivo hydrolysable ester and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to hereinabove.

The pharmaceutical compositions of this invention will normally be administered to humans so that, for example, a daily dose of 0.5 to 75 mg/kg body weight (and preferably of 0.5 to 30 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention.

Therefore in a further aspect, the present invention provides a compound of the formula (I) or a pharmaceutically acceptable salt or in vivo hydrolysable ester thereof for use in a method of therapeutic treatment of the human or animal body.

In yet a further aspect the present invention provides a method of treating a disease condition mediated by TNF which comprises administering to a warm-blooded animal an effective amount of a compound of the formula (I) or a pharmaceutically acceptable salt or in vivo hydrolysable ester thereof. The present invention also provides the use of a compound of the formula (I) or a pharmaceutically acceptable salt or in vivo hydrolysable ester thereof in the preparation of a medicament for use in a disease condition mediated by TNF.

In another aspect the present invention provides a process for preparing a compound of the formula (I) or a pharmaceutically acceptable salt or in vivo hydrolysable ester thereof which process comprises a) reacting a compound of the formula (III):

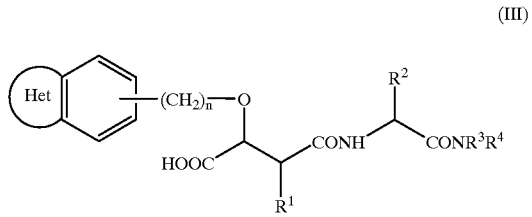

(III)

wherein n, Het, $R^1$–$R^4$ are as hereinbefore defined, or an activated derivative thereof with hydroxylamine, O-protected hydroxylamine or a salt thereof; or b) coupling a compound of the formula (IV) with a compound of the formula (V):

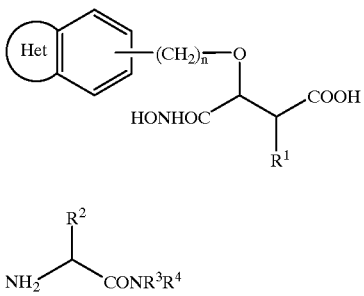

(IV)

(V)

wherein n. Het. $R^1$–$R^4$ are as hereinbefore defined, under standard peptide coupling conditions: or c) reacting a compound of the formula (VI) with compound of the formula (VII):

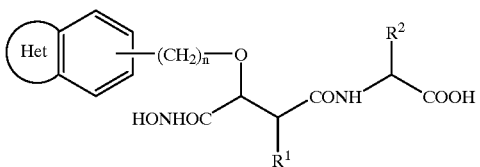

(VI)

$HNR^3R^4$ (VII)

wherein n, Het, R–$R^4$ are as hereinbefore defined, under standard peptide coupling conditions:

wherein any functional group is protected, if necessary, and:
i. removing any protecting groups;
ii. optionally forming a pharmaceutically acceptable salt or in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming silanol (the said alcohol or silanol preferably containing 1–20 carbon atoms.

Examples of carboxy protecting groups include straight or branched chain (1–12C) alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg benzyl, p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2–6C) alkenyl groups (eg allyl and vinylethyl).

Methods particularly appropriate for the removal of carboxyl protecting groups include for example acid-, base-, metal- or enzymically-catalysed hydrolysis.

Examples of hydroxyl protecting groups include lower alkyl groups (eg t-butyl), lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups.

Examples of amino protecting groups include formyl, aralkyl groups (eg benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl); trialkylsilyl (eg trimethylsilyl and t-butyldimethylsilyl); alkyidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

The hydroxylamine group (HONH—), in particular in process variants (b) and (c), is typically O-protected for example with benzyl, t-butyl or a silyl group.

The compound of the formula (III) may be reacted in the form of the acid or an activated derivative thereof such as an acid halide, acid anhydride or an 'activated' ester such as 1H-benzo[1,2,3]triazol-1-yl, 1-hydroxy-benzo[1,2,3] triazole, pentafluorophenyl or 2,4,5-trichlorophenyl. The reaction of the compound of the formula (III) and hydroxylamine is performed under standard conditions. Typically the reaction of an activated ester of a compound of the formula (III) and hydroxylamine or O-protected hydroxylamine is performed in the presence of a base, for example 2,6-lutidine in an anhydrous aprotic solvent, for example dimethylformamide, at a non-extreme temperature, for example in the region −30° to +25°, preferably about 0° C.

The compound of the formula (III) may be prepared by reacting a compound of the formula (VIII):

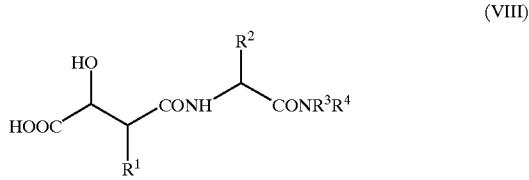

(VIII)

wherein $R^1$–$R^4$ are as hereinbefore defined and preferably the carboxylic acid is protected: with a compound of the formula (IX):

L-(CH$_2$)$_n$-Het  (IX)

wherein L is a leaving group and n and Het are as hereinbefore defined.

L is a leaving group for example halo such as chloro or bromo or a sulphonyloxy group such as methanesulphonyloxy, trifluoromethanesulphonyloxy or p-toluenesulphonyloxy.

Typically the reaction of the compounds (VIII) and (IX) is carried out in the presence of a base, for example sodium hydride, in an anhydrous aprotic solvent for example dimethylformamide or tetrahydrofuran, at a non-extreme temperature for example at ambient temperature.

The compounds of the formula (IX) are prepared according to standard methods of organic chemistry.

The compounds of the formula (VIII), preferably in carboxy-protected from, are prepared by reacting a compound of the formula (V) with a compound of the formula (X):

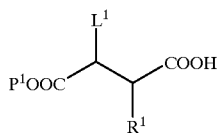

(X)

wherein $P^1$ is a carboxy-protecting group, $R^1$ is as hereinbefore defined and $L^1$ is a leaving group. Suitably $L^1$ is a leaving group such as halo, for example chloro, bromo or iodo, or a sulphonyloxy group, such as $C_{1-6}$alkanesulphonyloxy for example methanesulphonyloxy, benzenesulphonyloxy or 4-methylbenzenesulphonyloxy.

The reaction between the compounds of the formulae (V) and (X) is conveniently performed at a non-extreme temperature for example –25° C. to +50° C. and more conveniently 0° C. to +30° C. and most conveniently at ambient temperature.

The reaction is typically performed in a substantially inert organic solvent for example an aprotic solvent such as acetonitrile or diethyl ether.

The reaction of the compounds of the formulae (V) and (X) is believed to proceed via the formation of the lactone of the formula (XI)

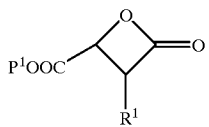

(XI)

wherein $P^1$ and $R^1$ are as hereinbefore defined.

The compound of the formula (V) acts as a base which is believed to convert the carboxylic acid function of the compound of the formula (X) to a carboxylate anion and which then displaces the leaving group $L^1$ to form the lactone. The lactone is believed to be ring-opened by nucleophilic attack of the compound of the formula (V) to form the compound of the formula (VIII).

In another aspect a compound of the formula (XI) may be prepared by reacting a compound of the formula (X) with a non-nucleophilic base. In this way the base converts the carboxylic acid function of the compound of the formula (III) to a carboxylate anion which displaces $L^1$ to form the lactone. However the non-nucleophilic base does not substantially react further with the lactone which may be isolated and then reacted with a compound of the formula (V).

Suitable non-nucleophilic bases include both organic and inorganic bases.

Preferably the base is an inorganic base such as an alkali metal or alkaline earth metal carbonate or bicarbonate for example sodium bicarbonate, potassium carbonate, sodium carbonate or potassium bicarbonate. Suitably the reaction is performed under biphasic conditions with the compound of the formula (X) dissolved in an aprotic organic solvent such as acetonitrile, diethyl ether or dichloromethane which is stirred, typically vigorously, with an aqueous solution of the base at a non-extreme temperature for example an ambient temperature. The reaction may be monitored by thin layer chromatography or any other convenient methodology and, after a suitable period of time, the organic phase may be separated and worked-up to provide the compound of the formula (XI). In an alternative the reaction is performed in the presence of a phase transfer catalyst for example benzyl trimethylammonium chloride, against with stirring at a non-extreme temperature.

In an alternative the non-nucleophilic base, for reacting with a compound of the formula (X), may be an organic base for example a tertiary amine such as di-isopropylethylamine. The reaction of a non-nucleophilic organic base with a compound of the formula (X) is typically performed under standard conditions.

The compounds of the formula (X) may be prepared by reacting a dianion of the formula (XII);

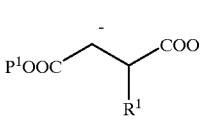

(XII)

wherein $P^1$ and $R^1$ are as hereinbefore defined, with a source of the group $L^1$.

Suitable source of halo include carbon tetrachloride and carbon tetrabromide.

Typically the dianion of the formula (XII) is formed by reacting the corresponding neutral compound with a non-nucleophilic base, for example lithium di-isopropylamide at low temperatures (–78° C.) to form the dianion which is then reacted with the source of the group $L^1$.

The neutral compounds corresponding to the formula (XII) are known in, or may be made, by the methods of the literature.

In an alternative the compounds of the formula (VIII) may be prepared by reacting a compound of the formula (XIII) with a compound of the formula (VII):

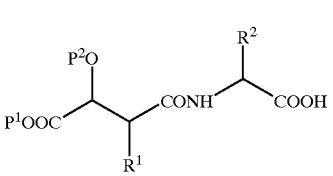

(XIII)

wherein $P^1$, $R^1$–$R^4$ are as hereinbefore defined and $P^2$ is a hydroxy protecting group under standard peptide coupling conditions and deprotecting as necessary. Conveniently $P^1$ and $P^2$ may be linked, for example to form an acetal ring.

The compounds of the formula (XIII) may be prepared by reacting a compound of the formula (X) with an optionally carboxy-protected compound of the formula (XIV):

$$NH_2CHR^2COOH \quad (XIV)$$

wherein $R^2$ is as hereinbefore defined under standard peptide coupling conditions and subsequently protecting the carboxy group as necessary. The compound of the formula (X) may be formed in situ from the compound of the formula (XI).

The compounds of the formula (I) may also be prepared by reacting compounds of the formulae (IV) and (V) as hereinbefore defined. This reaction is typically performed under standard peptide coupling conditions. The compounds of the formula (IV) may be prepared by reacting hydroxylamine, O-protected by hydroxylamine or a salt thereof with a compound of the formula (XV).

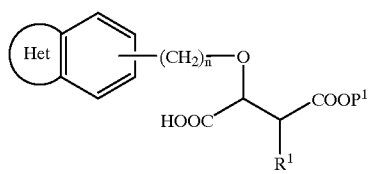

(XV)

wherein $R^1R^1$, n and Het are as hereinbefore defined, in a manner analogous to that described for reacting a compound of the formula (III), and thereafter deprotecting as necessary.

The compounds of the formula (I) may also be prepared by reacting compounds of the formula (VI) and (VII) as hereinbefore defined, typically under standard peptide coupling conditions. The compounds of the formula (VI) may be prepared by reacting hydroxylamine, O-protected hydroxylamine or a slat thereof with a compound of the formula (XVI):

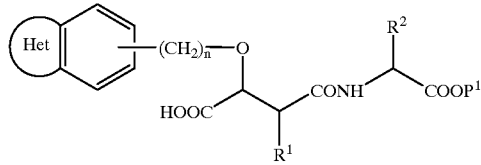

(XVI)

wherein $P^1$, n, $R^1$, $R^2$ and Het are hereinbefore defined in a manner analogous to that described for reacting a compound of the formula (III) and subsequently deprotecting as necessary.

The compounds of the formula (XVI) may be prepared by reacting a hydroxy-deprotected compound of the formula (XIII) with a compound of the formula (IX).

The following biological test methods, data and Examples serve to illustrate the present invention.

Isolated Enzyme Assay

The ability of the compounds of this invention to inhibit proTNFα convertase enzyme is assessed a partially purified, isolated enzyme assay, the enzyme being obtained from the membranes of THP-1 cells.

Assessment in human cell line (THF-2)

The ability of the compounds of this invention in inhibit TNFα production is assessed in THP-1 cells which are a human myelomonocytic cell line which synthesise and secrete TNFα when stimulated with lipopolysaccharide.

THP-1 cells ($4 \times 10^5$ cells in 160 µl medium RPMI1640+ bicarbonate, penicillin, streptomycin and glutamine) are incubated with 20 µl of test compounds (triplicates) in DMSO or appropriate vehicle, in a 96 well tissue culture (TC) plate, for 30 min at 37° C. in a humidified (5% $CO_2$/95°/oair) incubator, prior to addition of 20 µl lipopolysaccharide (LPS) (E. coli. 0111:B4 (Sigma); final concentration 50 µg/ml). Each assay includes controls of THP-1 cells incubated with medium alone (six wells/plate) or with a standard TNFα inhibitor. The plates are then incubated for 6 hours at 37° C. (humidified incubator) after which time 100 µl samples are removed from each well and transfered to a 96 well plate for storage at −70° C. for subsequent analysis of TNFα concentration by ELISA. In this test, generally, compounds are of interest if they have activity below 10 µM.

Assessment in whole blood assay

The ability of the compounds of this invention to inhibit TNFα production is also assessed in a human whole blood assay (HWBA). Human whole blood secretes TNFα when stimulated with LPS. This property of blood forms the basis of an assay which is used as a secondary test for compounds which profile as active in the THP-1 test. Heparinized (10Units/ml) human blood obtained from volunteers is diluted 1:5 with medium (RPM11640+bicarbonate, penicillin, streptomycin and glutamine) and incubated (160 µl) with 20 µl of test compound (triplicates), in DMSO or appropriate vehicle, for 30 min at 37° C. in a humidified (5%$CO_2$/95%/air) incubator, prior to addition of 20 µl LPS (E. coli. 0111:B4; final concentration 10 µg/ml). Each assay includes controls of diluted blood incubated with medium alone (6 wells/plate) or a known TNFα inhibitor as standard. The plates are then incubated for 6 hours at 37° C. (humidified incubator), centrifuged (2000 rpm for 10 min; 4° C.), plasma harvested (50–100 µl) and stored in 96 well plates at −70° C. before subsequent analysis for TNFα concentration by ELISA. In this test, generally, compounds are of interest if they have activity below 50 µM.

In vivo assessment

The ability of the compounds of this invention as ex vivo TNFα inhibitors is assessed in the rat. Briefly, groups of male Wistar Alderly Park (AP) rats (180–210 g) are dosed with compound (6 rats) or drug vehicle (10 rats) by the appropriate route e.g. peroral (p.o.), intraperitoneal (i.p.), subcutaneous (s.c.). Ninety minutes later rates are sacrificed using a rising concentration of $CO_2$ and bled out via the posterior vena cavae into 5 Units of sodium heparin/ml blood. Blood samples are immediately placed on ice and centrifuged at 2000 rpm for 10 min at 4° C. and the harvested plasmas frozen at −20° C. for subsequent assay of their effect on TNFα production by LPS-stimulated human blood. The rat plasma samples are thawed and 175 µl of each sample are added to a set format pattern in a 96U well plate. Fifty µl of heparinized human blood is then added to each well, mixed and the plate is incubated for 30 min at 37° C. (humidified incubator). LPS (25 µl; final concentration 10 µg/ml) is added to the wells and incubation continued for a further 5.5 hours. Control wells are incubated with 25 µl of medium alone. Plates are then centrifuged for 10 min at 2000 rpm and 200 µl of the supernatant are transferred to a 96 well plate and frozen at −20° C. for subsequent analysis of TNF concentration by ELISA.

Data analysis by dedicated software calculates for each compound/dose:

$$\text{Percent inhibition of } TNF\alpha = \frac{\text{Mean } TNF\alpha(\text{Controls}) - \text{Mean } TNF\alpha(\text{Treated}) \times 100}{\text{Mean } TNF\alpha \text{ (Controls)}}$$

Pharmacodynamic test

To evaluate the clearance properties of the compounds of this invention a sensitive ex vivo pharmacodynamic test is employed which utilises the CON2 assay to evaluate clearance rate.

This is a generic test which can be used to estimate the clearance rate of compounds across a range of species. Animals (eg. rats, marmosets) are dosed iv with a soluble formulation of compound and at subsequent time points (e.g., 5, 10, 15, 20, 30, 45, 60, 120 min) blood samples are taken from an appropriate vessel in to 10U heparin. Plasma fractions are obtained following centrifugation and the plasma proteins precipitated with ethanol (70%) final concentration). After 30 mins at 4° C. the plasma proteins are sedimented by centrifugation and the supernatant fraction is evaporated to dryness using a Savant speed vac. The sediment is reconstituted in CON2 assay buffer and subsequently analysed for compound content using the TNF convertase assay (CON2). Briefly, a compound concentration-response curve is constructed for the compound undergoing evaluation. Serial dilutions of the reconstituted plasma extracts are assessed for activity and the amount of compound present in the original plasma sample is calculated using the concentration-response curve taking into account the total plasma dilution factor.

Test as anti-arthritic agent

Activity of a compound as an anti-arthritic is tested as follows. Acid soluble native type II collagen was shown by Trentham et al. [1] to be arthritogenic in rats: it caused polyarthritis when administered in Freunds incomplete adjuvant. This is now known as collagen-induced arthritic (CIA) and similar condition can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritic clinical trials indicate that TNF plays a major role in this chronic inflammatory disease. Thus CIA in DBA/1 mice as described in references 2 and 3 is a tertiary model which can be used to demonstrate the anti-arthritic activity of a compound.

1. Trentham, D. E. et al., (1977) J. Exp. Med., 146, 857.
2. Williams, R. O. et al., (1992) Proc Natl. Acad Sci, 89, 9784.
3. Williams, R. O. et al., (1995) Immunology, 84, 433.

In the examples:
(a) NMR spectra were taken at 400 MHz.
(b) DMF means dimethylflormamide;
(c) Evaporation of solvents was carried out under reduced pressure;
(d) LDA means lithium di-isopropylamide;
(e) THF means tetrahydrofuran;
(f) DMSO means dimethylsulphoxide;
(g) AcOH means acetic acid.

EXAMPLE 1

$N^2$-[4-(N-Hydroxyamino)-2R-isobutyl-3S-(1'-methyl-2'-oxo-1',2'-dihydroquinonline-6'-yl) methoxysuccinyl]-L-tert-leucine-$N^1$-methylamide

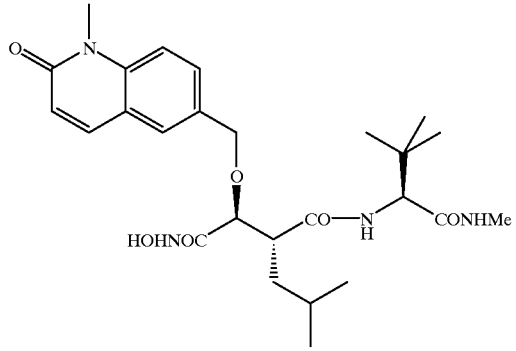

$N^2$-[4-Hydroxy-2R-isobutyl-3S-(1'-methyl-2'-oxo-1',2'-dihydroquinolin-6'-yl)methoxysuccinyl]-L-tert-leucine-$N^1$-methylamide (435 mg, 0.89 mmol) was dissolved in DMF (8 ml). 1-Hydroxybenzotriazole (180 mg, 1.35 mmol) was added, followed by N-ethyl-N'-(3-dimethylaminopropyl) carbodiimide hydrochloride (256 mg, 1.35 mmol), 2,6-lutidine (207 μl, 1.78 mmol) and O-(tert-butyl dimethylsilyl) hydroxylamine (180 mg, 1.16 mmol). The resulting solution was stirred at room temperature overnight. The crude reaction mixture was treated with HCl (2N, 1.5 ml) and purified by C18 preparative HPLC using as eluant a mixture of acetonitrile and water/1% AcOH (gradient from 1/9 to 35/65). Elution yielded the title compound (200 mg, 45% yield) as a white solid : m.p.=160–169° C.;

$^1$H-NMR (DMSO $d_6$): 0.79 (d, 3H, J=6.2 Hz), 0.81 (s, 9H), 0.85 (d, 3H, J=6.2 Hz), 0.91 (m, 1H), 1.32–149 (m, 2H), 2.56 (d, 3H, J=4.4 Hz), 2.95 (m, 1H), 3.62 (s, 3H), 3.8 (d, 1H, J=9.5 Hz), 4.20 (d, 1H, J=9.1 Hz), 4.32 (d, 1H, J=11.7 Hz), 4.51 (d, 1H, J=11.7 Hz), 6.64 (d, 1H, J=9.1 Hz), 7.48 (m, 2H), 7.59 (s, 1H), 7.7–7.8 (m, 2H), 7.82 (d, 1H, J=9.5 Hz), 9.11 (s, 1H), 10.87 (s, 1H),; MS (ESI): 525 (M+Na$^+$) and 541 (M+K$^+$).

$N^2$-[4-Hydroxy-2R-isobutyl-3S-(1'-methyl-2'-oxo-1',2'-dihydroquinoline-6'-yl)methoxysuccinyl]-L-tert-leucine-$N^1$-methylamide used as the starting material was obtained as follows:

(i) $N^2$-[3S-Hydroxy-2R-isobutyl-4-tert-butyloxysuccinyl]-L-tert-leucine-$N^1$-methylamide (400 mg, 1.07 mmol) was dissolved in THF (10 ml), under argon. Sodium hydride (50 mg, 60% in oil, 1.2 mmol) was added followed 3 minutes later by a solution of 6-bromomethyl-1-methyl-2-oxo-1,2-dihydroquinoline $^{Ref\ 1}$ (325 mg, 1.3 mmol) in THF (10 ml) and sodium iodide (161 mg, 1.07 mmol). The resulting mixture was stirred at room temperature overnight. The mixture was treated with a saturated solution of NH$_4$Cl and extracted with ethyl acetate. The combined organic extracts were dried over MgSO$_4$, filtered and the solvents were removal. The residue was purified by flash chromatography on silica using acetonitrile-dichloromethane (gradient from 3/7 to 3/2) as eluant to give $N^2$-[2R-isobutyl-3S-(1'-methyl-2'-oxo-1',2'-dihydroquinolin-6'-yl)methoxy-4-tert-butyloxysuccinyl]-L-tert-leucine-N'-methylamine (469 mg, 81%) as a foam : MS (ESI) : 544 (M+H') and 566 (M+Na$^+$).

ii) Trifluoroacetic acid (1.38 ml) was added dropwise to a solution of $N^2$-[2R-isobutyl-3S-(1'-methyl-2'-oxo-1',2'- dihydroquinolin-6'-yl)methoxy-4-tert-butyloxysuccinyl]-L-tert-leucine-$N^{1'}$-methylamide (489 mg, 0.9 mmol) in dry dichloromethane (2 ml). The solution was stirred at room temperature overnight. The solvent were evaporated in vacuo. The residue was taken up in toluene and the solvent was removed in vacuo (three times). The residue was taken up in diethyl ether, triturated and filtered to give $N^2$-[4-hydroxy-2R-isobutyl-3S-(1'-methyl-2'-oxo-1',2'-dihydroquinoline-6'-yl)methoxysuccinyl]-L-tert-leucine-$N^1$-methylamide (440 mg, 100%) : MS (ESI) : 488 (M+H$^+$) and 510 (M+Na$^+$).

$N^2$-[3S-hydroxy-2R-isobutyl-4-tert-butyloxysuccinyl]-L-tert-leucine-$N^1$-methylamide used as starting material for step (i) was obtained as follows:

a) To a stirred solution of LDA [45.5 mmol; prepared by addition of 2.5 M n-butyl lithium (18.2 ml, 45.5 mmol) in hexane to a solution of diisopropylamine (6.3 ml, 48.3 mmol) in dry THF (20 ml) at −78° C.] cooled to −78° C. under argon was added dropwise a solution of 2R-isobutyl-butan-1,4-dionic acid-4-tert-butyl ester $^{Ref\ 2}$ (5.0 g., 21.7 mmol) in dry THF (15 ml). The mixture was stirred for 45 minutes at −78° C. and a solution of cabon tetrachloride (2.3 ml, 23.9 mmol) in dry THF (3 ml) was added slowly, dropwise over ca. 8 minutes avoiding that the internal temperature rise above −65° C. The mixture was allowed to stir at −78° C. for 30 minutes, warmed to room temperature and stirred for one hour at room temperature. The solution was cooled to −78° C. and quenched by addition of HCl (2N, 3.3 ml). The solution was warmed to room temperature and extracted with diethyl ether. The combined organic extracts were dried over MgSO$_4$, filtered and the solvents were removed to give directly one crude single isomer. The residue was purified by flash chromatography on silica using acetonitrile as eluant to give 3R-chloro-2S-isobutyl-butan-1,4-dioic acid-4-tert-butyl ester (5.6 g, 98%) as a pale brown oil:

$^1$H-NMR (CDCl$_3$); 0.94 (d, 3H, J=4.8 Hz), 0.95 (d, 3H, J=4.8 Hz), 1.48 (s, 9H), 1.55 (m, 1H), 1.65–1.8 (m, 2H), 3.05–3.1 (m, 1H), 4.41 (d, 1H, J=8.1 Hz); MS (EI): 264 (M{$^{35}$Cl}+H$^+$) and 266 (M{$^{32}$Cl}+H$^+$).

b) To a stirred solution of 3R-chloro-2S-isobutyl-butan-1,4-dioic acid-4-tert-butyl ester (4.0 g, 15 mmol) in acetonitrile (100 ml) was added L-tert-leucine N-methylamide (2.8 g, 19.4 mmol). The mixture was stirred at room temperature for 24 hours. A further quantity of acetonitrile (25 ml) was added and the mixture stirred for 12 hours. The solvents were evaporated in vacuo and the residue partitioned between water and ethyl acetate. The combined organic extracts were dried over MgSO$_4$, filtered and the solvents were removed. The residue was purified by flash chromatography on silica using acetonitrile-dichloromethane (gradient from ¼ to ⅓) as eluant to give $N^2$-[3S-hydroxy-2R-isobutyl-4-tert-butyloxysuccinyl]-L-tert-leucine-$N^1$-methylamide (2.48 g, 45%) as a beige solid:

$^1$H-NMR (CDCl$_3$): 0.92 (d, 3H, J=6.2 Hz), 0.96 (d, 3H, J=6.2 Hz), 0.99 (s, 9H), 1.47 (s, 9H), 1.55–1.75 (m, 3H), 2.75 (m, 1H), 2.79 (d, 3H, J=5.1 Hz), 3.73 (d, 1H, J=5.9 Hz), 4.1 (m, 1H), 4.13 (d, 1H, J=8.8 Hz), 5.88 (m, 1H), 6.68 (d, 1H, J=9.1 Hz);

MS (EI): 373 (M+H$^+$)

A small quantity of unreacted 3R-chloro-2S-isobutyl-butan-1,4-dioic acid-4-tert-butyl ester (336 mg) was recovered from the chromatography.

EXAMPLE 2

$N^2$-[4-(N-Hydroxyamino)-2R-isobutyl-3S-(quinolin-8'-yl)methoxysuccinyl]-L-tert-leucine-$N^1$-methylamide.

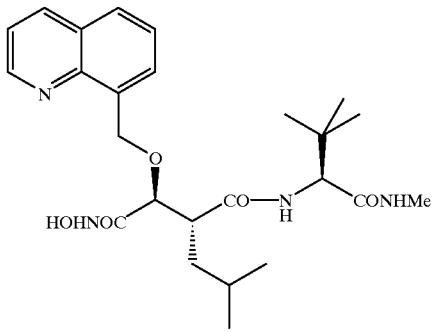

In a manner analogous to that described in the first paragraph of Example 1, from $N^2$-[4-hydroxy-2R-isobutyl-3S-(quinolin-8'-yl)methoxysuccinyl]-L-tert-leucine-$N^1$-methylamide (425 mg, 0.92 mmol) there was obtained the title compound (280 mg, 65%) as a white solid: m.p. 118–121° C.;

$^1$H-NMR (DMSO d$_6$): 0.80 (s, 9H), 0.81 (d, 3H, J=6.2 Hz), 0.87 (d, 3H, J=6.2 Hz), 1.0 (m, 1H), 1.37–1.52 (m, 2H), 2.55 (d, 3H, J=4.8 Hz), 3.04 (m, 1H), 3.97 (d, 1H, J=9.2 Hz), 4.17 (d, 1H, J=9.2 Hz), 4.93 (d, 1H, J=13.9 Hz), 5.14 (d, 1H, J=13.9 Hz), 7.53–7.60 (m, 2H), 7.76–7.91 (m, 4H), 8.4 (m, 1H), 8.89 (m, 1H), 9.1 (s br, 1H), 11.2 (s br, 1H); MS (ESI): 473 (M+H$^+$) and 495 (M+Na$^+$).

The starting material was prepared as follows:

(i) In a manner analogous to that described in Example 1 (i), from $N^2$-[3S-hydroxy-2R-isobutyl-4-tert-butyloxysuccinyl]-L-tert-leucine-$N^1$-methylamide (500 mg, 1.34 mmol) and 8-iodomethylquinole $^{Ref\ 3}$ (430 mg, 1.6 mmol) except that no sodium iodide was added, there was obtained $N^2$-[2R-isobutyl-3S-(quinolin-8'-yl)methoxy-4-tert-butyloxysuccinyl]-L-tert-leucine-$N^1$-methylamide (540 mg, 79%) as a gum:

MS (ESI): 514 (M+H$^+$) and 536 (M$^+$Na$^+$).

(ii) In a manner analogous to that described in Example 1 (ii), from $N^2$-[2R-isobutyl-3S-(quinolin-8'-yl)methoxy-4-tert-butyloxysuccinyl]-L-tert-leucine-$N^1$-methylamide (540 mg, 1.05 mmol) there was obtained $N^2$-[4-hydroxy-2R-isobutyl-3S-(quinolin-8'-yl)methoxysuccinyl]-L-tert-leucine-$N^1$-methylamide (432 mg, 94.5%) as a white solid: MS (ESI): 458 (M+H$^+$) and 480 (M+Na$^+$).

EXAMPLE 3

N²-[4(N-Hydroxyamino)-2R-isobutyl-3S-(2'-methyl-4'-oxo-3',4'-dihydroquinazolin-6'-yl)methoxysuccinyl]-L-tert-leucine-N¹-methylamide.

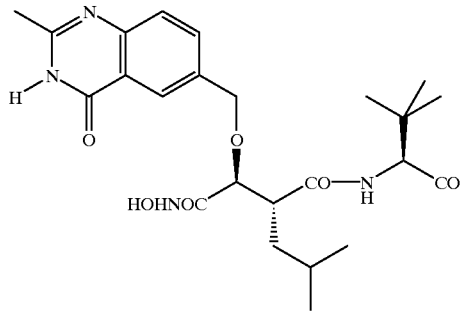

In a manner analogous to that described in the first paragraph of Example 1, from N²-[4-hydroxy-2R-isobutyl-3S-(2'-methyl-4'-oxo-3',4'-dihydroquinazolin-6'-yl)methoxysuccinyl]-L-tert-leucine-N¹-methylamide (470 mg, 0.96 mmol) there was obtained the title compound (152 mg, 32%) as a white solid: m.p.=180–187° C.;

¹H-NMR (DMSO d₆): 0.76 (s, 9H), 0.78 (d, 3H, J=6.6 Hz), 0.84 (d, 3H, J=6.6 Hz), 0.89 (m, 1H), 1.3–1.45 (m, 2H), 2.35 (s, 3H), 2.56 (d, 3H, J=4.4 Hz), 2.97 (m, 1H), 3.81 (d, 1H, J=9.5 Hz), 4.16 (d, 1H, J=9.1 Hz), 4.34 (d, 1H, J=11.7 Hz), 4.5 (d, 1H, J=11.7 Hz), 7.49 (d, 1H, J=8.4 Hz), 7.63 (dd, 1H, J=8.4 Hz, J=1.8 Hz), 7.68–7.74 (m, 2H), 7.96 (d, 1H, J=1.47 Hz), 9.12 (s br, 1H), 10.91 (s br, 1H), 12.16 (br, 1H); MS (ESI): 526 (M+Na⁺).

The starting material was prepared as follows:

(i) In a manner analogous to that described in Example 1 (i), from N²-[3S-hydroxy-2R-isobutyl-4-tert-butyloxysuccinyl]-L-tert-leucine-N¹-methylamide (650 mg, 1.7 mmol) and 6-bromomethyl-2-methyl-4-oxo-3,4-dihydroquinazoline $^{Ref\ 4}$ (663 mg, 2.55 mmol) except that 15-crown-5 (1 drop) was also added, there was obtained N²-[2R-isobutyl-3S-(2'-methyl-4'-oxo-3',4'-dihydroquinazolin-6'-yl)methoxy-4-tert-butyloxysuccinyl]-L-tert-leucine-N¹-methylamide (530 mg, 57%) as a foam:

MS (EI): 545 (M+H⁺).

(ii) In a manner analogous to that described in Example 1 (ii), from N²-[2R-isobutyl-3S-(2'-methyl-4'-oxo-3',4'-dihydroquinazolin-6'-yl)methoxy-4-tert-butyloxysuccinyl]-L-tert-leucine-N¹-methylamide (530 mg, 0.97 mmol) there was obtained N²-[4-hydroxy-2R-isobutyl-3S-(2'-methyl-4'-oxo-3',4'-dihydroquinazolin-6'-yl)methoxysuccinyl]-L-tert-leucine-N¹-methyl amide (480 mg, 100%):

MS (ESI): 489 (M+H⁺) and 511 (M+Na⁺).

EXAMPLE 4

N²-[4-(N-Hydroxyamino)-2R-isobutyl-3S-(7'-bromo-2'-methyl-4'-oxo-3',4'-dihydroquinazolin-6'-yl)methoxysuccinyl]-L-tert-leucine-N¹-methylamide.

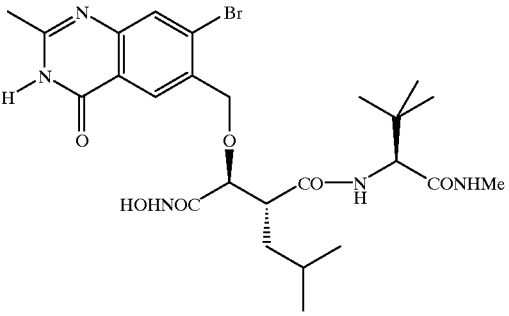

In a manner analogous to that described in the first paragraph of Example 1, from N²-[4-hydroxy-2R-isobutyl-3S-(7'-bromo-2'-methyl-4'-oxo-3',4'-dihydroquinazolin-6'-yl)methoxy succinyl]-L-tert-leucine-N¹-methylamide (345 mg, 0.6 mmol) there was obtained the title compound (140 mg, 40%) as a white powder:

m.p.=184–188° C.;

¹H-NMR (DMSO d₆): 0.72 (s, 9H), 0.8 (d, 3H, J=6.6 Hz), 0.86 (d, 3H, J=6.6 Hz), 0.9 (m, 1H), 1.32–1.45 (m, 2H), 2.35 (s, 3H), 2.55 (d, 3H, J=4.4 Hz), 3.12 (m, 1H), 3.9 (d, 1H, J=9.9 Hz), 4.14 (d, 1H, J=9.5 Hz), 4.44 (d, 1H, J=12.8 Hz), 4.53 (d, 1H, J=13.2 Hz), 7.7 (m, 1H), 7.78 (s, 1H), 7.83 (d, 1H, J=9.15 Hz), 8.17 (s, 1H), 9.15 (s br, 1H), 11.0 (s br, 1H), 12.3 (s br 1H); MS (ESI): 582 (M{⁷⁹Br}+H⁺) and 584 (M{⁸¹Br}+H⁺).

The starting material was prepared as follows:

(i) In a manner analogous to that described in Example 1(i), from N²-[3S-hydroxy-2R-isobutyl-4-tert-butyloxysuccinyl]-L-tert-leucine-N¹-methylamide (470 mg, 1.26 mmol) and 7-bromo-6-bromomethyl-2-methyl-4-oxo-3,4-dihydroquinazoline (500 mg, 1.5 mmol) except that 15-crown-5 (1 drop) was also added, there was obtained N²-[2R-isobutyl-3S-(7'-bromo-2'-methyl-4'-oxo-3',4'-dihydroquinazolin-6'-yl)methoxy-4-tert-butyloxysuccinyl]-L-tert-leucine-N¹-methylamide (500 mg, 64%) as a foam:

MS (ESI): 645 (M{⁷⁹Br}+Na⁺) and 647 (M{⁸¹Br}+Na⁺).

(ii) In a manner analogous to that described in Example 1 (ii), from N²-[2R-isobutyl-3S-(7'-bromo-2'-methyl-4'-oxo-3',4'-dihydroquinazolin-6'-yl)methoxy-4-tert-butyloxysuccinyl]-L-tert-leucine-N¹-methylamide (500 mg, 0.8 mmol) there was obtained N²-[4-hydroxy-2R-isobutyl-3S-(7'-bromo-2'-methyl-4'-oxo-3',4'-dihydroquinazolin-6'-yl)methoxysuccinyl]-L-tert-leucine-N¹-methyl amide (387 mg, 85%):

MS (ESI): 567 (M{⁷⁹Br}+H⁺) and 569 (M{⁸¹Br}+H⁺).

7-Bromo-6-bromomethyl-2-methyl-4l-oxo-3,4-dihydroquinazoline was prepared by standard deprotection (aq. HCl) of (7-bromo-6-bromomethyl-2-methyl-4-oxo-3,4-dihydroquinazoline-3-yl)methyl 2,2-dimethylpropanoate [RN 140395-66-0; Zeneca Ltd.; (Pegg, S. J., Wardleworth, J. M.) UK Pat. Appl., GB 2264946 A1].

EXAMPLE 5

N²-[4-(N-Hydroxyamino)-2R-isobutyl-3S-(1'-methyl-2'-oxo-1',2'-dihydroquinolin-6'-yl)methoxysuccinyl]-L-tert-leucine-N¹-dimethylamide.

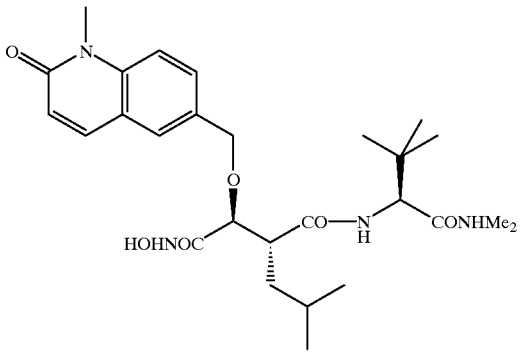

In a manner analogous to that described in the first paragraph of Example 1, from N²-[4-hydroxy-2R-isobutyl-3S-(1'-methyl-2'-oxo-1',2'-dihydroquinolin-6'-yl)methoxysuccinyl]-L-tert-leucine-N¹-dimethylamide (205 mg, 0.4 mmol) there was obtained the title compound (116 mg, 56%) as a white solid:

m.p.=160–166° C.; ¹H-NMR (DMSO d₆): 0.78 (d, 3H, J=6.6 Hz), 0.83 (d, 3H, J=6.6 Hz), 0.86 (s, 9H), 0.9 (m, 1H), 1.3–1.45 (m, 2H), 2.81 (s, 3H), 2.99 (m, 1H), 3.08 (s, 3H), 3.63 (s, 3H), 3.81 (d, 1H, J=9.9 Hz), 4.33 (d, 1H, J=11.7 Hz), 4.51 (d, 1H, J=11.7 Hz), 4.76 (d, 1H, J=9.2 Hz), 6.64 (d, 1H, J=9.5 Hz), 7.5 (m, 2H), 7.6 (s, 1H), 7.84 (m, 2H), 9.1 (s br, 1H), 10.89 (s br, 1H); MS (ESI): 517 (M+H⁺) and 539 (M+Na⁺).

The starting material was prepared as follows:

(i) In a manner analogous to that described in Example 1 (i), from N²-[3S-hydroxy-2R-isobutyl-4-tert-butyloxysuccinyl]-L-tert-leucine-N¹-dimethylamide (197 mg, 0.51 mmol) and 6-bromomethyl-1-methyl-2-oxo-1,2-dihydroquinoline (141 mg, 0.56 mmol) there was obtained N²-[2R-isobutyl-3S-(1'-methyl-2'-oxo-1',2'-dihydroquinolin-6'-yl)methoxy-4-tert-butyloxysuccinyl]-L-tert-leucine-N¹-dimethylamide (243 mg, 85%) as a gum:

MS (EI): 558 (M+H⁺) and 580 (M+Na⁺).

(ii) In a manner analogous to that described in Example 1 (ii), from N²-[2R-isobutyl-3S-(1'-methyl-2'-oxo-1',2'-dihydroquinolin-6'-yl)methoxy-4-tert-butyloxysuccinyl]-L-tert-leucine-N¹-dimethylamide (242 mg, 0.43 mmol) there was obtained N²-[4-hydroxy-2R-isobutyl-3S-(1'-methyl-2'-oxo-1',2'-dihydroquinolin-6'-yl)methoxysuccinyl]-L-tert-leucine-N¹-dimethyl amide (210 mg, 97%) as a white solid: MS (ESI): 502 (M+H⁺) and 524 (M+Na⁺).

N²-[3S-Hydroxy-2R-isobutyl-4-tert-butyloxysuccinyl]-L-tert-leucine-N¹-dimethylamide used as starting material for step (i) was obtained as follows:

In a manner analogous to that described in Example 1 (b), to a solution of 3R-chloro-2S-isobutyl-butan-1,4-dioic acid-4-tert-butyl ester (500 mg, 1.89 mmol) in acetonitrile (7 ml) was added L-tert-leucine N-dimethylamide^NOTE (448 mg, 2.83 mmol). The mixture was stirred at room temperature for 24 hours. The mixture was poured into aqueous NH₄Cl (10%) and extracted with ethyl acetate. The combined organic extracts were washed with water, dried over MgSO₄, filtered and the solvents were removed. The residue was purified by a flash chromatography on silica using acetonitrile-dichloromethane (¼) as eluant to give N²-[3S-hydroxy-2R-isobutyl-4-tert-butyloxysuccinyl]-L-tert-leucine-N¹-dimethylamide (395 mg, 54%) as a gum which solidified:

¹H-NMR (CDCl₃): 0.92 (d, 3H, J=5.5 Hz), 0.95 (d, 3H, J=5.8 Hz), 0.98 (s, 9H), 1.47 (s, 9H), 1.55–1.7 (m, 3H), 2.72 (m, 1H), 2.95 (s, 3H), 3.1 (s, 3H), 3.86 (s br, 1H), 4.07 (m, 1H), 4.86 (d, 1H, J=9.5 Hz), 6.61 (d, 1H, J=9.2 Hz); MS (EI): 409 (M+Na⁺).

^NOTE L-tert-leucine N-dimethylamide was prepared by the reaction of L-tert-leucine with triphosgene to give 3-(S)-tert-butyl oxazolidine-1,4-dione which was then treated with a saturated ethereal solution of dimethylamine.

EXAMPLE 6

N²-[4-(N-Hydroxyamino)-2R-isobutyl-3S-(1'-methyl-2'-oxo-1',2'-dihydroquinolin-6'-yl)methoxysuccinyl]-L-tert-leucine-N¹-(2-dimethylaminoethyl)amide.

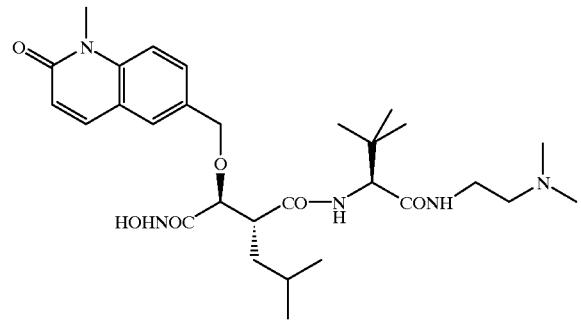

In a manner analogous to that described in the first paragraph of Example 1, from N²-[4-hydroxy-2R-isobutyl-3S-(1'-methyl-2'-oxo-1',2'-dihydroquinolin-6'-yl)methoxysuccinyl]-L-tert-leucine-N¹-(2-dimethylaminoethyl)amide (230 mg, 0.35 mmol) there was obtained the title compound (60 mg, 50%) as a white solid:

m.p.=95–102° C.; ¹H-NMR (DMSO d₆+TFA): 0.79 (d, 3H, J=6.4 Hz), 0.84 (s, 9H), 0.86 (d, 3H, J=6.6 Hz), 1.0 (m, 1H), 1.41 (m, 2H), 2.81 (s, 6H) 3.0–3.2 (m, 3H), 3.3–3.45 (m, 2H), 3.62 (s, 3H), 3.8 (d, 1H, J=9.5 Hz), 4.11 (m, 1H), 4.4 (m, 2H), 6.64 (d, 1H J=9.5 Hz), 7.45–7.9 (m, 4H), 8.2 (m, 2H), 9.4 (s br, 1H). MS (ESI): 560 (M+H⁺).

The starting material was prepared as follows:

(i) In a manner analogous to that described in Example 1 (i), from N²-[3S-hydroxy-2R-isobutyl-4-tert-butyloxysuccinyl]-L-tert-leucine-N¹-(2-dimethylaminoethyl)amide (220 mg, 0.51 mmol) and 6-bromomethyl-1-methyl-2-oxo-1,2-dihydroquinoline (142 mg, 0.56 mmol) there was obtained N²-[2R-isobutyl-3S-(1'-methyl-2'-oxo-1',2'-dihydroquinolin-6'-yl)methoxy-4-tert-butyloxysuccinyl]-L-tert-leucine-N¹-(2-dimethylaminoethyl)amide (132 mg, 43%): MS (EI): 601 (M+H⁺).

(ii) In a manner analogous to that described in Example 1 (ii), from N²-[2R-isobutyl-3S-(1'-methyl-2'-oxo-1',2'-dihydroquinolin-6'-yl)methoxy-4-tert-butyloxysuccinyl]-L-tert-leucine-N¹-(2-dimethylaminoethyl)amide (230 mg, 0.38 mmol) there was obtained N²-[4-hydroxy-2R-isobutyl-3S-(1'-methyl-2'-oxo-1',2'-dihydroquinolin-6'-yl)methoxysuccinyl]-L-tert-leucine-N¹-(2-dimethylaminoethyl)amide (240 mg, 96%) as a hygroscopic solid:

MS (ESI): 545 (M+H⁺).

N²-[3S-Hydroxy-2R-isobutyl-4-tert-butyloxysuccinyl]-L-tert-leucine-N¹-(2-dimethylaminoethyl)amide used as starting material for step (i) was obtained as follows:

In a manner analogous to that described in Example 1 (b), to a solution of 3R-chloro-2S-isobutyl-butan-1,4-dioic acid-4-tert-butyl ester (500 mg, 1.89 mmol) in acetonitrile (7 ml) was added L-tert-leucine N-(2-dimethylaminoethyl)amide$^{NOTE}$ (455 mg, 2.2 mmol). The mixture was stirred at room temperature for 48 hours. The mixture was poured into aqueous NH₄Cl (10%) and extracted with ethyl acetate. The combined organic extracts were washed with water, dried over MgSO₄, filtered and the solvents were removed. The residue was purified by flash chromatography on silica using methanol-dichloromethane (⅛) as eluant to give N²-[3S-hydroxy-2R-isobutyl-4-tert-butyloxysuccinyl]-L-tert-leucine-N¹-(2-dimethylaminoethyl)amide(437 mg, 54%) as a gum:

¹H-NMR (CDCl₃): 0.93 (d, 3H, J=5.8 Hz), 0.96 (d, 3H, J=6.2 Hz), 1.0 (s, 9H), 1.48 (s, 9H), 1.55–1.71 (m, 3H), 2.23 (s, 6H), 2.46 (m, 2H), 2.76 (m, 1H), 3.34 (m, 2H), 4.11 (d, 1H, J=3.3 Hz), 4.19 (d, 1H, J=9.2 Hz), 6.6 (m, 2H); MS (EI): 430 (M+H⁺) and 452 (M+Na⁺).

$^{NOTE}$ L-tert-leucine 2-dimethylaminoethylamide was prepared by the reaction of L-tert-leucine with triphosgene to give 3-(S)-tert-butyl oxazolidine-1,4-dione which was then treated with N,N-dimethyl ethylenediamine.

EXAMPLE 7

N²-[4-(N-Hydroxyamino)-2R-(4'-benzyloxy)butyl-3S-(1'-methyl-2'-oxo-1',2'-dihydroquinolin-6'-yl)methoxysuccinyl]-L-tert-leucine-N¹-methylamide.

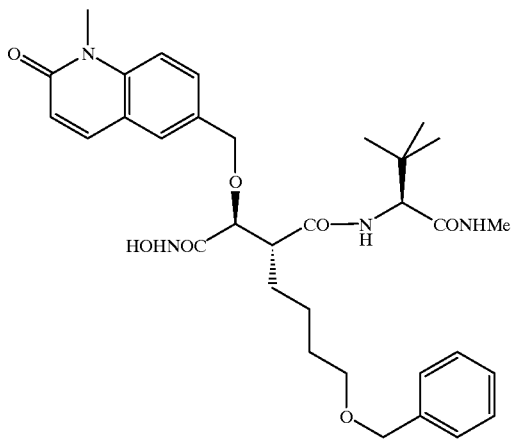

In a manner analogous to that described in the first paragraph of Example 1, from N²-[4-hydroxy-2R-(4'-benzyloxy)butyl-3S-(1'-methyl-2'-oxo-1',2'-dihydroquinolin-6'-yl)methoxysuccinyl]-L-tert-leucine-N¹-methylamide (300 mg, 0.5 mmol) there was obtained the title compound (145 mg, 47%) as a white solid: m.p.= 188–190° C.;

¹H-NMR (CDCl₃): 0.86 (s, 9H), 1.39–1.45 (m, 2H), 1.5–1.8 (m, 4H), 2.89 (d, 3H, J=4.39 Hz), 3.05–3.1 (m, 1H), 3.41 (t, 2H, J=6.23 Hz), 3.7 (s, 3H), 3.94 (d, 1H, J=9.2 Hz), 4.1 (d, 1H, J=3.3 Hz), 4.45 (d, 2H, J=1.5 Hz), 4.5 (d, 1H, J=11.0 Hz), 4.96 (d, 1H, J=11.0 Hz), 6.72 (d, 1H, J=9.5 Hz), 6.95–7.0 (m, 1H), 7.25–7.38 (m, 6H), 7.55 (d, 1H, J=8.8 Hz), 7.61 (dd, 1H, J=8.4 Hz, J=1.8 Hz), 7.65 (d, 1H, J=9.5 Hz), 7.69 (d, 1H, J=1.5 Hz), 9.6 (s br, 2H); MS (ESI): 609 (M+H⁺) and 631 (M+Na⁻).

The starting material was prepared as follows:

(i) In a manner analogous to that described in Example 1 (i), from N²-[3S-hydroxy-2R-(4'-benzyloxy)butyl-4-tert-butyloxysuccinyl]-L-tert-leucine-N¹-methylamide (480 mg, 1.0 mmol) and 6-bromomethyl-1-methyl-2-oxo-1,2-dihydroquinoline (278 mg, 1.1 mmol) there was obtained N²-[2R-(4'-benzyloxy)butyl-3S-(1'-methyl-2'-oxo-1',2'-dihydroquinolin-6'-yl)methoxy-4-tert-butyloxysuccinyl]-L-tert-leucine-N¹-methylamide (402 mg, 61%) as a white solid: MS (EI): 650 (M+H⁺) and 672 (M+Na⁺).

(ii) In a manner analogous to that described in Example 1 (ii), from N²-[2R-(4'-benzyloxy)butyl-3S-(1'-methyl-2'-oxo-1',2'-dihydroquinolin-6'-yl)methoxy-4-tert-butyloxysuccinyl]-L-tert-leucine-N¹-methylamide (380 mg, 0.58 mmol) there was obtained N²-[4-hydroxy-2R-(4'-benzyloxy)butyl-3S-(1'-methyl-2'-oxo-1',2'-dihydroquinolin-6'-yl)methoxysuccinyl]-L-tert-leucine-N¹-methylamide (335 mg, 97%) as a fine white powder:

MS (ESI): 594 (M+H⁺) and 616 (M+Na⁺).

N²-[3S-Hydroxy-2R-(4'-benzyloxy)butyl-4-tert-butyloxysuccinyl]-L-tert-leucine-N¹-methylamide used as starting material for step (i) was obtained as follows:

In a manner analogous to that described in Example 1 (a), to a stirred solution of LDA [11.24 mmol; prepared by addition of 2.5 M n-butyl lithium (4.5 ml, 11.24 mmol) in hexane to a solution of diisopropylamine (1.57 ml, 11.24 mmol) in dry THF (4 ml) at −78° C.] cooled to −78° C. under argon was added dropwise a solution of 2R-(4'-benzyloxy)butyl-butan-1,4-dioic acid-4-tert-butyl ester$^{Ref\,5}$ (1.8 g, 5.35 mmol) in dry THF (2 ml). The mixture was stirred for 70 minutes at −78° C. and a solution of carbon tetrachloride (0.566 ml, 5.89 mmol) in dry THF (1 ml) was added slowly, dropwise over ca. 8 minutes avoiding that the internal temperature rise above −65° C. The mixture was allowed to stir at −78° C. for 60 minutes and quenched by addition of HCl (2N). The solution was warmed to room temperature and extracted with diethyl ether. The combined organic extracts were dried over MgSO₄, filtered and the solvents were removed to give directly crude 3R-chloro-2S-(4'-benzyloxy)butyl-butan-1,4-dioic acid-4-tert-butyl ester (2.13 g, 100%) as a brown oil used as such in the following step:

¹H-NMR (CDCl₃): 1.3–1.75 (m, 6H), 1.47 (s, 9H), 3.04 (m, 1H), 3.47 (t, 2H, J=6.3 Hz), 4.37 (d, 1H, J=9.1 Hz), 4.49 (s, 2H), 7.29–7.34 (m, 5H); MS (EI): 371 (M{³⁵Cl}+H⁺) and 373 (M{³⁷Cl}+H⁺).

In a manner analogous to that described in Example 1 (b), to a solution of 3R-chloro-2S-(4'-benzyloxy)butyl-butan-1,4-dioic acid-4-tert-butyl ester (1.9 g, 512 mmol) in acetonitrile (40 ml) was added L-tert-leucine N-methylamide (738 mg, 6.15 mmol). The mixture was stirred at room temperature for 16 hours. The mixture was poured into aqueous NH₄Cl (10%) and extracted with ethyl acetate. The combined organic extracts were washed with water, dried over MgSO₄, filtered and the solvents were removed. The residue was purified by flash chromatography on silica using acetonitrile-dichloromethane (gradient from 3/17 to 7/13) as eluant to give N²-[3S-hydroxy-2R-(4'-benzyloxy)butyl-4-tert-butyloxysuccinyl]-L-tert-leucine-N¹-methylamide (520 mg, 27%) as a pale brown gum:

¹H-NMR (CDCl₃): 0.98 (s, 9H), 1.46 (s, 9H), 1.6–1.9 (m, 6H), 2.66 (m, 1H), 2.77 (d, 3H, J=4.8 Hz), 3.46 (t, 2H, J=6.3 Hz), 3.74 (s br, 1H), 4.12 (m, 2H), 4.49 (m, 2H), 5.79 (m, 1H), 6.71 (d, 1H, J=9.2 Hz) 7.33–7.36 (m, 5H);

MS (EI): 479 (M+H⁺).

A quantity of unreacted 3R-chloro-2S-(4'-benzyloxy) butyl-butan-1,4-dioic acid-4-tert-butyl ester (412 mg) was recovered from the chromatography.

EXAMPLE 8

N²-[4(N-Hydroxyamino)-2R-isobutyl-3S-(quinolin-8'-yl)methoxysuccinyl]-L-tert-leucine-N¹-dimethylamide

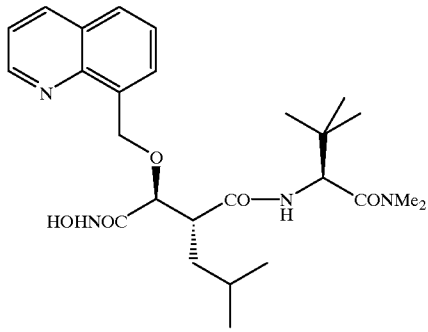

In a manner analogous to that described in the first paragraph of Example 1, from N²-[4-hydroxy-2R-isobutyl-3S-(quinolin-8'-yl)methoxy succinyl]-L-tert-leucine-N¹-dimethylamide (150 mg, 0.31 mmol) there was obtained the title compound (48 mg, 32%) as a white solid: m.p.= 145–151° C.

¹H-NMR (DMSO d₆): 0.78 (d, 3H, J=6.6 Hz), 0.83 (s, 9H), 0.84 (d, 3H), 1.0 (m, 1H), 1.35–1.5 (m, 2H), 2.77 (s, 3H), 3.04 (s, 3H), 3.06 (m, 1H), 3.94 (d, 1H, J=9.5 Hz), 4.72 (d, 1H, J=9.2 Hz), 4.90 (d, 1H), 5.13 (d, 1H), 7.5–7.6 (m, 2H), 7.8–7.95 (m, 3H), 8.38 (m, 1H), 8.89 (m, 1H), 9.1 (s, 1H), 11.18 (s, 1H); MS (ESI): 487 (M+H⁺) and 509 (M+Na⁺).

The starting material was prepared as in Example 5 using 8-iodomethylquinoline as alkylating agent.

EXAMPLE 9

N²-[4-(N-Hydroxyamino)-2R-isobutyl-3S-(quinolin-8'-yl)methoxysuccinyl]-L-tert-leucine-N¹-(2-dimethylaminoethyl)amide

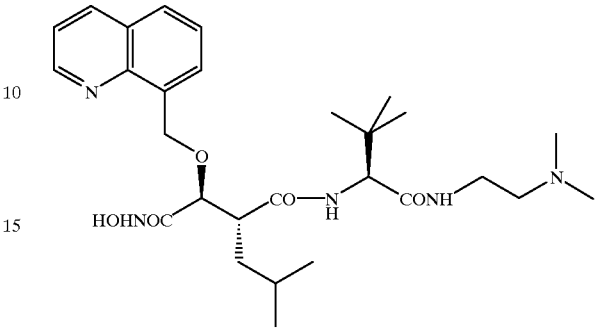

In a manner analogous to that described in the first paragraph of Example 1, from N²-[4-hydroxy-2R-isobutyl-3S-(quinolin-8'-yl)methoxysuccinyl]-L-tert-leucine-N¹-(2-dimethylaminoethyl)amide (384 mg, 0.5 mmol) there was obtained the title compound (115 mg, 39%) as a white solid: m.p.=85–90° C.;

¹H-NMR (DMSO d₆): 0.79 (d, 3H), 0.80 (s, 9H), 0.86 (d, 3H, J=6.2 Hz), 0.97 (m, 1H), 1.35–1.55 (m, 2H), 3.0–3.3 (m, 5H), 3.32 (s, 6H), 3.95 (d, 1H, J=9.5 Hz), 4.16 (d, 1H, J=8.8 Hz), 4.91 (d, 1H), 5.12 (d, 1H), 7.5–7.6 (m, 2H), 7.8–7.9 (m, 4H), 8.38 (d, 1H, J=6.6 Hz), 8.88 (dd, 1H, J=1.8 Hz, J=4.0 Hz), 9.1 (s, br, 1H), 11.2 (s, br, 1H);

MS (ESI): 530 (M+H⁺).

The starting material was prepared for Example 6 using 8-iodomethylquinoline as alkylating agent.

EXAMPLE 10

N²-[4-(N-Hydroxyamino)-2R-isobutyl-3S-(4'-oxo-3', 4'-dihydroquinazolin-6'-yl)methoxysuccinyl]-L-tert-leucine-N¹-methylamide

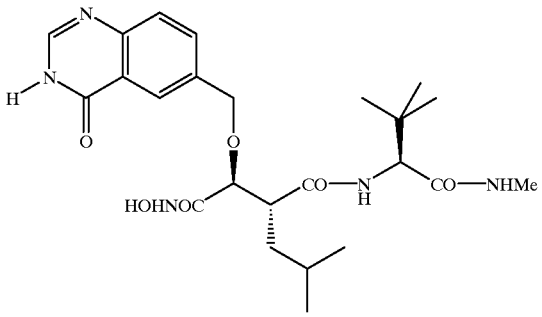

In a manner analogous to that described in the first paragraph of Example 1, from N²-[4-hydroxy-2R-isobutyl-3S-(4'-oxo-3',4'-dihydroquinazolin-6'-yl)methoxysuccinyl]-L-tert-leucine-N¹-methylamide (60 mg, 0.12 mmol) there was obtained the title compound (20 mg, 34%) as a white amorphous solid: m.p.=162–165° C.;

¹H-NMR (DMSO d₆): 0.74 (s, 9H), 0.77 (d, 3H, J=6.6 Hz), 0.83 (d, 3H, J=6.2 Hz), 0.89 (m 1H), 1.3–1.5 (m, 2H), 2.53 (d, 3H, J=4.4 Hz), 3.0 (m, 1H), 3.8 (d, 1H, J=9.9 Hz), 4.15 (d, 1H, J=9.5 Hz), 4.36 (d, 1H), 4.53 (d, 1H), 7.58 (d, 1H, J=8.4 Hz), 7.65–7.75 (m, 3H), 8.0 (d, 1H, J=1.8 Hz), 8.06 (s, 1H), 9.1 (s, br, 1H), 11.1 (s, br, 1H), 11.8 (s, br, 1H);

MS (ESI): 490 (M+H$^+$) and 512 (M+Na$^+$).

The starting material was prepared as in Example 3, using as alkylating agent 6-bromomethyl-4-oxo-3,4-dihydroquinazoline (prepared by bromination (NBS, AIBN in refluxing CCl$_4$) of 6-methylquinazolin-4-one (RN 19181-53-4; commercially availabile from Maybridge).

EXAMPLE 11

N$^2$-[4-(N-Hydroxyamino)-2R-(4'-benzyloxy)butyl-3S-(quinolin-8'-yl)methoxysuccinyl]-L-tert-leucine-N$^1$-methylamide

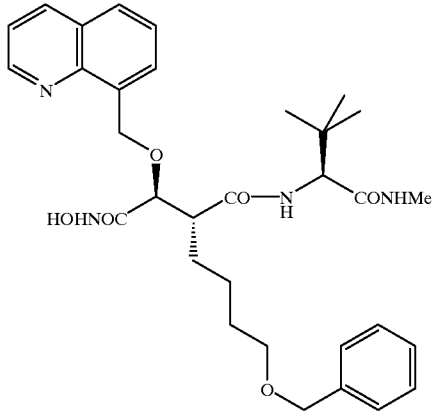

In a manner analogous to that described in the first paragraph of Example 1, from N$^2$-[4-hydroxy-2R-(4'-benzyloxy)butyl)-3S-(quinolin-8'-yl)methoxy succinyl]-L-tert-leucine-N$^1$-methylamide (250 mg, 0.44 mmol) there was obtained the title compound (110 mg, 43%) as a white solid: m.p.=92–94° C.;

$^1$H-NMR (CDCl$_3$): 0.64 (s, 9H), 1.4–1.46 (m, 2H), 1.58–1.66 (m, 2H), 1.73–1.79 (m, 2H), 2.74 (d, 3H, J=4.88 Hz), 2.84–2.89 (m, 1H), 3.44 (t, 2H, J=6.35 Hz), 3.99 (d, 1H, J=9.1 Hz), 4.34 (d, 1H, J=4.6 Hz), 4.46 (s, 2H), 4.68 (d, 1H), 5.43 (d, 1H), 6.08 (s, br, 1H), 6.85 (d, 1H, J=8.8 Hz), 7.31 (m, 5H), 7.51–7.56 (m, 2H), 7.68 (dd, 1H, J=7.1 Hz, J=1.2 Hz), 7.88 (dd, 1H, J=8.2 Hz, J=1.1 Hz), 8.27 (dd, 1H, J=8.3 Hz, J=1.7 Hz), 9.06 (dd, 1H, J=4.4 Hz, J=1.7 Hz), 114.2 (s, 2H);

MS (ESI): 579 (M+H$^+$).

The starting material was prepared as in Example 7 using 8-iodemethylquinoline as alkylating agent.

EXAMPLE 12

N$^2$-[4-(N-Hydroxyamino)-2R-(3'-benzyloxy) propyyl-3S-(2'-methyl-4'-oxo-3',4'-dihydroquinazolin-6'-yl)methylsuccinyl]-L-tert-leucine-N$^1$-methylamide.

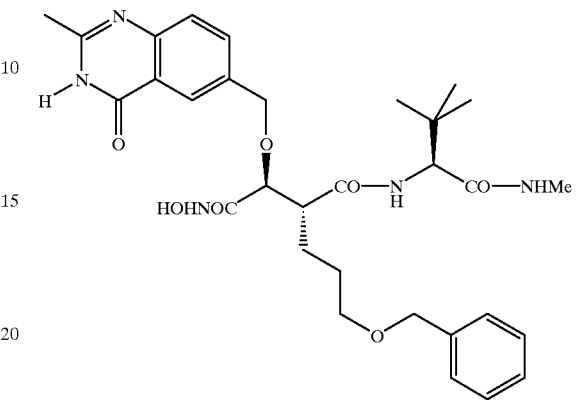

In a manner analogous to that described in the first paragraph of Example 1, except that O-(2,4-dimethoxybenzyl)hydroxylamine was used instead of O-(tert-butyldimethylsilyl)hydroxylamine and the reaction mixture was treated with 5% TFA/dichloromethane instead of HCl (2N), from N$^2$-[4-hydroxy-2R-(3'-benzyloxy)propyl-3S-(2'-methyl-4'-oxo-3',4'-dihydroquinazolin-6'-yl) methoxysuccinyl]-L-tert-leucine-N$^1$-methylamide (1.0 g, 1.7 mmol) there was obtained the title compound (430 mg, 41%) as a white solid: m.p.=189–194° C.;

$^1$H-NMR (DMSO d$_6$): 0.77 (s, 9H), 1.2–1.5 (m, 4H), 2.33 (s, 3H), 2.53 (d, 3H, J=4.4 Hz), 2.93 (m, 1H), 3.32 (m, 2H), 3.86 (d, 1H, J=9.9 Hz), 4.17 (d, 1H, J=9.2 Hz), 4.34 (d, 1H), 4.40 (s, 2H), 4.5 (d, 1H), 7.25–7.36 (m, 5H), 7.47 (d, 1H, J=8.4 Hz), 7.61 (d, 1H, J=8.1 Hz), 7.79 (m, 2H), 7.93 (s, 1H), 9.1 (s, 1H), 10.9 (s, 1H), 14.2 (s, 1H);

MS (ESI): 596 (M+H$^+$) and 618 (M+Na$^+$).

The starting material was prepared in a manner analogous to Example 7 using 6-bromomethyl-2-methyl-4-oxo-3,4-dihydroquinazoline as alkylating agent.

The 3R-chloro-2S-(3'-benzyloxy)propyl-butan-1,4-dioic acid-4-tert-butyl ester was prepared from 2R-(3'-benzyloxy) propan-butan-1,4-dioic acid-4-tert-butyl ester $^{Ref5}$ in a manner analogous to Example 7.

EXAMPLES 13–22

General Procedure

For Examples, 13–22 the final two steps were accomplished as described specifically in Example 13, by alkylation and subsequent deprotection of N$^2$-[4-(N-2',4'-dimethyloxybenzyloxy-N-2',4',6'-trimethoxybenzylamino)-3S-hydroxy-2R-isobutylsuccinyl]-L-tert-leucine-N$^1$-methylamide which was obtained as follows from N$^2$-[3S-Hydroxy-2R-isobutyl-4-tert-butyloxysuccinyl]-L-tert-leucine-N$^1$-methylamide [described in Example 1, paragraphs a) and b)].

N²-[4-(N-2',4'-Dimethoxybenzyloxy-N-2',4',6'-trimethoxybenzylamino)-3S-hydroxy-2R-isobutylsuccinyl]-L-tert-leucine-N¹-methylamide

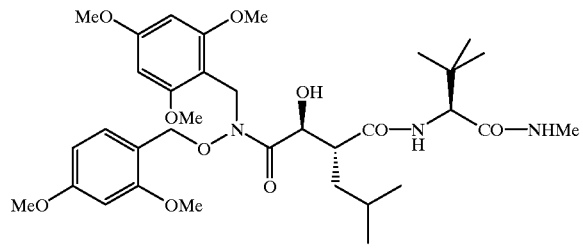

i) Trifluoroacetic acid (40 ml) was added dropwise to a solution of N²-[3S-hydroxy-2R-isobutyl-4-tert-butylsuccinyl]-L-tert-leucine-N¹-methylamide (10.2 g, 27.4 mmol) in dry dichloromethane (40 ml). The solution was stirred at room temperature overnight. The solvents were evaporated in vacuo. The residue was taken up in toluene and the solvent was removed in vacuo (three times). The residue was taken up in diethyl ether, triturated and filtered to give N²-[3S 3,4-dihydroxy-2R-isobutylsuccinyl]-L-tert-leucine-N¹-methylamide (8.6 g, 100%) MS (ESI): 317 (M+H⁺) and 339 (M+Na⁺).

ii) N²-[3S 3,4-dihydroxy-2R-isobutylsuccinyl]-L-tert-leucine-N¹-methylamide (8.0 g, 25.3 mmol) was dissolved in DMF (150 ml). 1-Hydroxybenzotriazole (5.1 g 37.9 mmol) was added followed by N-ethyl-N'-(3-dimethylaminoproply)carbodiimide hydrochloride (7.2 g 3.79 mmol), 2,6-lutidine (588 µl, 5 mmol) and O-(2,4-dimethoxybenzyl-N-2,4,6-trimethoxybenzyl) hydroxylamine (10.1 g, 27.8 mmol). The resulting solution was stirred at room temperature overnight. The crude reaction mixture was concentrated and partitioned between water and ethyl acetate. The combined organic extracts were washed with HCl (1N) brine, dried over MgSO₄, filtered and the solvents were removed. The residue was purified by flash chromatography on silica using acetonitrile-dichloromethane (2/3) as eluant to give the title compound (8.8 g, 53% yield) as a white solid:

¹H-NMR (CDCl₃): 0.7 (d, 3H, J=6.2 Hz), 0.81 0.8 (d, 3H, J=6.2 Hz), 1.04 (s, 9H), 1.37–1.64 (m, 3H), 2.69 (m, 1H), 2.79 (d, 3H, J=4.8 Hz), 3.37 (d, 1H, J=4.0 Hz), 3.76 (s, 6H), 3.79 (s, 6H), 3.83 (s, 3H), 4.12 (d, 1H, J=8.4 Hz), 4.52 (m, 1H), 4.81 (m, 2H), 4.89 (d, 1H, J=13.9 Hz), 5.14 (d, 1H, J=14.2 Hz), 6.14 (s, 2H), 6.4 (m, 2H), 6.85–7.0 (m, 3H).

EXAMPLE 13

N²-[4-(N-Hydroxyamino)-2R-isobutyl-3S-(1'-methyl-2'-oxo-1',2'-dihydroquinolin-7'-yl) methoxysuccinyl]- L-tert-leucine-N¹-methylamide

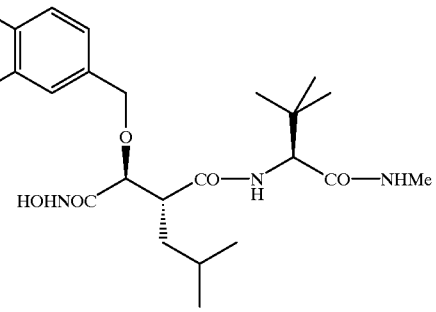

a) N²-[4-(N-2',4'-Dimethoxybenzyloxy-N-2',4',6'-trimethoxybenzylamine-3S-hydroxy-2R-isobutylsuccinyl]-L-tert-leucine-N¹-methylamide (330 mg, 0.5 mmol) was dissolved in dry THF (10 ml) under argon. Sodium hydride (23 mg, 60% in oil, 0.57 mmol) was added followed, 30 minutes later by 7-bromomethyl-1-methyl-2-oxo-1,2-dihydroquinoline ^Ref6 (138 mg, 0.54 mmol) sodium iodide (75 mg, 0.5 mmol) and one drop of 15-crown-5. The resulting mixture was stirred at room temperature overnight. The mixture was treated with a saturated solution of NH₄Cl and extracted with ethyl acetate. The combined organic extracts were dried over MgSO₄, filtered and the solvents were removed. The residue was purified by flash chromatography on silica using acetonitrile-dichloromethane (gradient from, 1/2 to 1/1) as eluent to give N²-[4-(N-2',4'-dimethoxybenzyloxy-N-2',4',6'-trimethoxybenzhylamino)-2R-isobutyl- 3S-(1'-methyl-2'-oxo-1',2'-dihydroquinolin-7'-yl)succinyl]-L-tert-leucine-N¹-methylamide (334 mg, 80%): MS (ESI): 833 (M+H⁺) and 855 (M+Na⁺).

b) Trifluoroacetic acid (0.8 ml) was added dropwise to a solution of N²-[4-(N-2',4'-dimethoxybenzyloxy-N-2',4',6'-trimethoxybenzylamino)-2R-isobutyl-3S-(1'-methyl-2'-oxo-1',2'-dihydroquinolin-7'-yl)succinyl]-L-tert-leucine-N¹-methylamide (300 mg, 0.36 mmol) in dry dichloromethane (7.2 ml). The solution was stirred at room temperature for 12 hours. The solvents were evaporated in vacuo. The residue was taken up in tolune and the solvent was removed in vacuo (three times). The residue was taken up in methanol, titrated and filtered to give the crude product which was purified by C18 preparative HPLC using as eluant a mixture of methanol and water/1% AcOH (1/1) to give the title compound (70 mg, 38%) as a white solid. m.p.=176–178° C.;

¹H-NMR (DMSO d₆): 0.76 (d, 3H, J=6.6 Hz), 0.81 (s, 9H), 0.83 (d, 3H, J=6.6 Hz), 0.9 (m, 1H), 1.4–1.6 (m, 2H), 2.54 (d, 3H, J=4.4 Hz), 2.95 (m, 1H), 3.63 (s, 3H), 3.81 (d, 1H, J=9.9 Hz), 4.20 (d, 1H, J=9.2 Hz), 4.4 (d, 1H), 4.6 (d, 1H), 6.59 (d, 1H, J=9.5 Hz), 7.15 (d, 1H), 7.39 (s, 1H), 7.64 (d, 1H, J=7.7 Hz), 7.77 (m, 2H), 7.88 (d, 1H, J=9.5 Hz), 9.1 (s, 1H), 10.9 (s, 1H); MS (ESI): 503 (M+H⁺) and 525 (M+Na⁺).

EXAMPLE 14

N²-[4-(N-Hydroxyamino)-2R-isobutyl-3S-(quinoxalin-5'-yl)methoxysuccinyl]-L-tert-leucine-N¹-methylamide

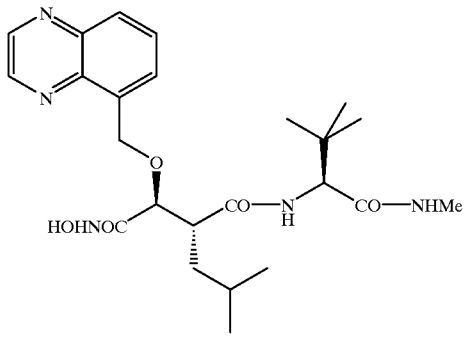

The general procedure of Example 13, using 5-Bromomethylquinoxaline $^{Ref7}$ as the alkylating agent was followed to give the title compound as a white solid. m.p.=170–174° C.;

¹H-NMR (DMSO d$_6$): 0.75 (s, 9H), 0.79 (d, 3H, J=6.2 Hz), 0.85 (d, 3H, J=6.2 Hz), 0.93 (m, 1H), 1.35–1.5 (m, 2H), 2.53 (d, 3H, J=4.4 Hz), 3.03 (m, 1H), 3.94 (d, 1H, J=9.9 Hz), 4.14 (d, 1H, J=9.5 Hz), 4.96 (d, 1H), 5.1 (d, 1H), 7.75–7.81 (m, 3H), 7.9 (d, 1H, J=7.3 Hz), 8.01 (d, 1H, J=8.4 Hz), 8.92 (d, 1H, J=1.8 Hz), 8.97 (d, 1H, J=1.8 Hz), 9.12 (s, 1H), 10.98 (s, 1H);

MS (ESI): 474 (M+H⁺) and 496 (M+Na⁺).

Purification: C18 preparative HPLC using as eluant a mixture of acetonitrile and water/1% AcOH (gradient from 1/5 to 1/1) to give the title compound (82 mg, 43%).

EXAMPLE 15

N²-[4-(N-Hydroxyamino)-2R-isobutyl-3S-(1'-methyl-2'-oxo-1',2'-dihydroquinolin-5'-yl)methoxysuccinyl]-L-tert-leucine-N¹-methlyamide.

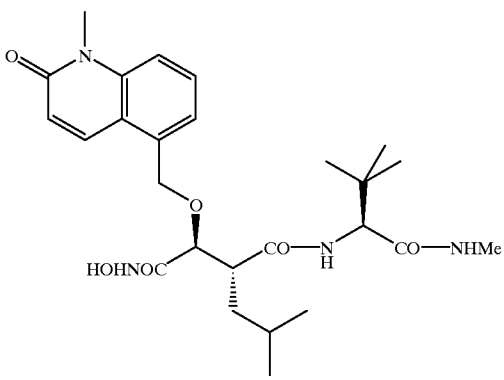

The general procedure of Example 13, using 5-Bromomethyl-1-methyl-2-oxo-1,2-dihydroquinoline $^{Ref8}$ as the alkylating agent was followed to give the title compound as a white solid. m.p.=198–200° C.;

¹H-NMR (DMSO d$_6$): 0.61 (s, 9H), 0.77 (d, 3H, J=6.6 Hz), 0.82 (d, 3H, J=6.6 Hz), 0.9 (m, 1H), 1.3–1.5 (m, 2H), 2.52 (d, 3H, J=4.7 Hz), 2.95 (m, 1H), 3.62 (s, 3H), 3.84 (d, 1H, J=9.5 Hz), 4.60 (d, 1H, J=9.2 Hz), 4.45 (d, 1H), 4.7 (d, 1H), 6.62 (d, 1H, J=9.9 Hz), 7.18 (d, 1H, J=5.9 Hz), 7.51–7.6 (m, 3H), 7.64 (m, 1H), 8.0 (d, 1H, J=9.5 Hz), 9.1 (s, br, 1H), 10.95 (s, 1H); MS (ESI): 503 (M+H⁺) and 525 (M+Na⁺);

Purification: filtration through C18 'bond-elute' column using as eluant a mixture of methanol and water/1% AcOH (3/2) to give the title compound (120 mg, 57%);

EXAMPLE 16

N²-[4-(N-Hydroxyamino)-2R-isobutyl-3S-(1'-methyl-2',3'-dioxoindolin-5'-yl)methoxysuccinyl]-L-tert-leucine-N¹-methylamide.

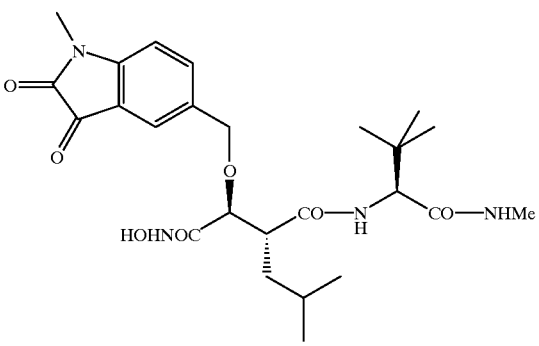

The general procedure of Example 13, using 5-Bromomethyl-1-methyl-2,3-dioxoindoline $^{Ref9}$ as the alkylating agent was followed to give the title compound as an orange solid. m.p.=142–145° C.;

¹H-NMR (DMSO d$_6$): 0.77 (d, 3H, J=6.6 Hz), 0.81 (s, 9H), 0.82 (d, 3H, J=6.6 Hz), 0.9 (m, 1H), 1.3–1.45 (m, 2H), 2.45 (d, 3H, J=4.4 Hz), 2.92 (m, 1H), 3.14 (s, 3H), 3.75 (d, 1H, J=9.2 Hz), 4.15 (d, 1H, J=9.5 Hz), 4.23 (d, 1H), 4.38 (d, 1H), 7.07 (d, 1H, J=8.1 Hz), 7.44 (s, 1H), 7.53 (d, 1H, J=8.1 Hz), 7.8–7.9 (m, 2H), 9.1 (s, br, 1H), 10.9 (s, br, 1H);

MS (ESI): 505 (M+H⁺) and 527 (M+Na⁺).

Purification: C18 preparative HPLC using as eluant a mixture of acetonitrile and water/1% AcOH (gradient from, 1/9 to 3/7) to give the title compound (10 mg, 34%).

EXAMPLE 17

N²-[4-(N-Hydroxyamino)-2R-isobutyl-3S-(1'-methyl-2'oxo-1',2',3',4'-tetrahydroquinolin-6'-yl)methoxysuccinyl]-L-tert-leucine-N¹-methylamide.

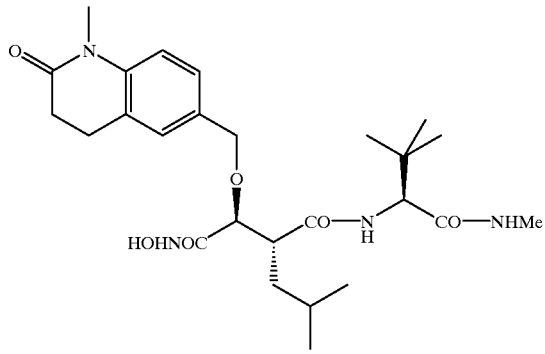

The alkylation step was carried out using 6-bromomethyl-1-methyl-2-oxo-1,2-dihydroquinoline, as in Example 1, and the intermediate was reduced with hydrogen over an Adam's catalyst to give 1,2,3,4-tetrahydroquinoline intermediate which was then deprotected as in Example 13. This provided the title compound as a white solid.

m.p.=148–150° C.;

¹H-NMR (DMSO d₆): 0.77 (d, 3H, J=6.2 Hz), 0.82 (s, 9H), 0.82 (d, 3H), 0.9 (m, 1H), 1.3–1.5 (m, 2H), 2.51 (m, 2H), 2.55 (d, 3H, J=4.4 Hz), 2.8 (m, 2H), 2.9 (m, 1H), 3.23 (s, 3H), 3.76 (d, 1H, J=9.9 Hz), 4.20 (m, 2H), 4.36 (d, 1H), 6.99 (d, 1H, J=8.1 Hz), 7.18 (m, 2H), 7.68 (d, 1H, J=9.5 Hz), 7.76 (m, 1H), 9.1 (s, br, 1H), 10.9 (s, br, 1H);

MS (ESI): 505 (M+H⁺) and 527 (M+Na⁺).

Purification: C18 preparative HPLC using as eluant a mixture of methanol and water/1% AcOH (gradient from 3/7 to 7/3) to give the title compound (146 mg, 53%).

EXAMPLE 18

N²-[4-(N-Hydroxyamino)-2R-isobutyl-3S-)quinoxalin-6'-yl)methoxysuccinyl]-L-tert-leucine-N¹-methylamide.

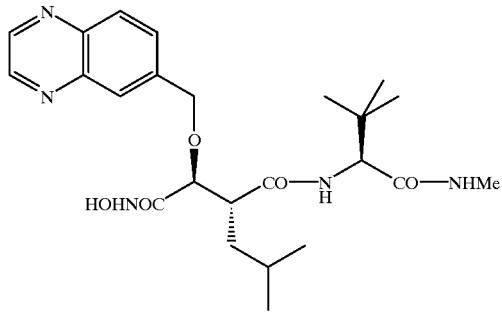

The general procedure of Example 13, using 6-Bromomethylquinoxaline$^{Ref10}$ as the alkylating agent was folowed to give the title compound as a white solid.

m.p.=156–160° C.;

¹H-NMR (DMSO d₆): 0.77 (s, 9H), 0.78 (d, 3H), 0.84 (d, 3H, J=6.2 Hz), 0.9 (m, 1H), 1.38–1.5 (m, 2H), 2.53 (d, 3H, J=4.8 Hz), 3.02 (m, 1H), 3.87 (d, 1H, J=9.9 Hz), 4.19 (d, 1H, J=9.2 Hz), 4.51 (d, 1H), 4.69 (d, 1H), 7.76 (m, 3H), 8.02 (m, 2H), 8.93 (m, 2H), 9.1 (s, br, 1H), 10.9 (s, br, 1H); MS (ESI): 474 (M+H⁺) and 496 (M+Na⁺).

Purification: C18 preparative HPLC using as eluant a mixture of acetonitrile and water/1% AcOH (gradient from 1/9 to 1/2) to give the title compound (87 mg, 34%).

EXAMPLE 19

N²-[4-(N-Hydroxyamino)-2R-isobutyl-3S-(2,3-dihydro-4-methyl-3-oxo-1,4-benzoaxazin-7-yl)methoxysuccinyl]-L-tert-leucine-N¹-methylamide.

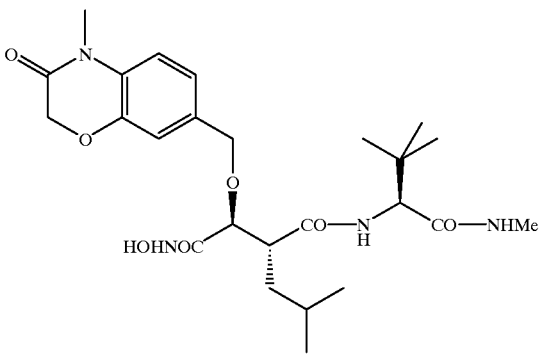

The general procedure of Example 13, using 7-Bromomethyl-2 3-dihydro-4-methyl-3-oxo-1 4-benzoaxazine$^{Ref11}$ as the alkylating agent was followed to give the title compound as a white solid. m.p.=132–138° C.;

¹H-NMR (DMSO d₆): 0.77 (d, 3H, J=6.2 Hz), 0.83 (d, 3H), 0.84 (s, 9H), 0.89 (m, 1H), 1.3–1.45 (m, 2H), 2.54 (d, 3H, J=4.4 Hz), 2.92 (m, 1H), 3.26 (s, 3H), 3.75 (d, 1H, J=9.5 Hz), 4.20 (m, 2H), 4.36 (d, 1H), 4.61 (s, 2H), 6.92 (m, 2H), 7.06 (d, 1H, J=8.1 Hz), 7.69 (d, 1H, J=9.5 Hz), 7.76 (m, 1H), 9.1 (s br, 1H), 10.83 (s, 1H); MS (ESI): 507 (M+H⁺) and 529 (M+Na⁺).

Purification: filtration through C18⁺ 'bond-elute' column using as eluant a mixture of methanol and water/1% AcOH (1/1) to give the title compound (155 mg, 64%);

EXAMPLE 20

N$^2$-[4-(N-Hydroxyamino)-2R-isobutyl-3S-(2'-oxo-1', 2'-dihydroquinolin-5'-yl)methoxysuccinyl]-L-tert-leucine-N$^1$-methylamide

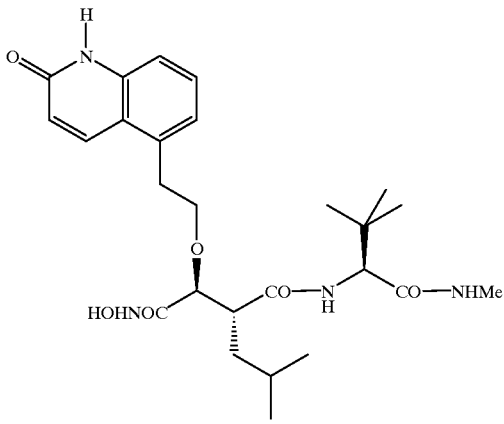

The general procedure of Example 13, using 5-Bromomethyl-2-oxo-1,2-dihydroquinoline$^{Ref\ 12}$ as alkylating agent [in the presence of 2 equivalents of base] was followed to give the title compound as a white solid.

$^1$H-NMR (DMSO d$_6$): 0.61 (s, 9H), 0.77 (d, 3H, J=6.6 Hz), 0.82 (d, 3H, J=6.2 Hz), 0.9 (m, 1H), 1.25–1.45 (m, 2H), 2.52 (d, 3H, J=4.8 Hz), 2.9 (m, 1H), 3.83 (d, 1H, J=9.5 Hz), 4.05 (d, 1H, J=9.2 Hz), 4.4 (d, 1H), 4.66 (d, 1H), 6.5 (d, 1H, J=9.9 Hz), 7.06 (d, 1H, J=6.9 Hz), 7.25 (d, 1H, J=8.4 Hz), 7.34 (t, 1H, J=7.3 Hz), 7.56 (d, 1H, J=9.1 Hz), 7.69 (m, 1H), 7.99 (d, 1H, J=9.9 Hz), 9.1 (s br, 1H), 10.9 (s br, 1H), 11.7 (s, 1H);

MS (ESI): 489 (M+H$^+$) and 511 (M+Na$^+$).

Purification: C18 preparative HPLC using as eluant a mixture of methanol and water/1% AcOH (gradient from 1/4 to 2/1) to give the title compound (112 mg, 37%).

EXAMPLE 21

N$^2$-[4-(N-Hydroxyamino)-2R-isobutyl-3S-(benzoxazol-5'-yl)methoxysuccinyl]-L-tert-leucine-N$^1$-methylamide

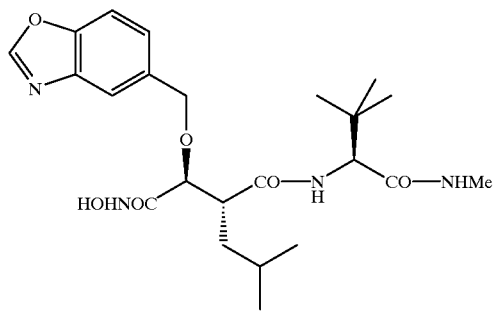

The general procedure of Example 13, using 5-Bromomethylbenzoxazole$^{Ref13}$ as the alkylating agent was followed to give the title compound as a white powder.

m.p.=120–124° C.;

$^1$H-NMR (DMSO d$_6$): 0.77 (d, 3H, J=6.2 Hz), 0.79 (s, 9H), 0.83 (d, 3H, J=6.2 Hz), 0.89 (m, 1H), 1.3–1.5 (m, 2H), 2.54 (d, 3H, J=4.4 Hz), 2.94 (d, 1H), 3.81 (d, 1H, J=9.9 Hz), 4.17 (d, 1H, J=9.5 Hz), 4.36 (d, 1H), 4.54 (d, 1H), 7.3 (d, 1H, J=8.4 Hz), 7.6–7.8 (m, 4H), 8.71 (s, 1H), 9.1 (s br, 1H), 10.9 (s br, 1H); MS (ESI): 463 (M+H$^+$) and 485 (M+Na$^+$).

Purification: C18 preparative HPLC using as eluant a mixture of acetonitrile and water/1% AcOH (gradient from 1/9 to 1/3) to give the title compound (22 mg, 17%).

EXAMPLE 22

N$^2$-[4-(N-Hydroxyamino)-2R-isobutyl-3S-(2'-methylbenzothiazol-5'-yl)methoxysuccinyl]-L-tert-leucine-N$^1$-methylamide

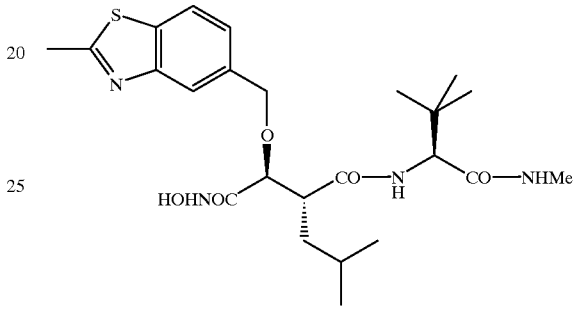

The general procedure of Example 13, using 5-Bromomethyl-2-methylbenzothiazole$^{Ref14}$ as the alkylating agent was followed to give the title compound as a white solid.

m.p.=133–136° C.;

$^1$H-NMR (DMSO d$_6$): 0.77 (d, 3H, J=6.6 Hz), 0.8 (s, 9H), 0.83 (d, 3H, J=6.6 Hz), 0.88 (m, 1H), 1.35–1.5 (m, 2H), 2.54 (d, 3H, J=4.4 Hz), 2.79 (s, 3H), 2.95 (m, 1H), 3.8 (d, 1H, J=9.5 Hz), 4.18 (d, 1H, J=9.2 Hz), 4.37 (d, 1H), 4.55 (d, 1H), 7.27 (d, 1H, J=8.4 Hz), 7.65–7.8 (m, 3H), 7.93 (d, 1H, J=8.1 Hz), 9.1 (s, 1H), 10.86 (s, 1H);

MS (ESI): 493 (M+H$^+$) and 515 (M+Na$^+$).

Purification: C18 preparative HPLC using as eluant a mixture of acetonitrile and water/1% AcOH (gradient from 1/9 to 1/3) to give the title compound (110 mg, 40%).

EXAMPLE 23

Typical tablet formulations for a compound of this invention or a pharmaceutically-acceptable salt thereof ('Compound X') are:

|  | mg/tablet |
|---|---|
| (a) Tablet Formulation I | |
| Compound X | 100 |
| Lactose Ph.Eur | 179 |
| Croscarmellose sodium | 12 |
| Polyvinylpyrrolidone | 6 |
| Magnesium stearate | 3 |

-continued

| (b) Tablet Formulation II | mg/tablet |
|---|---|
| Compound X | 250 |
| Lactose Ph.Eur | 215 |
| Croscarmellose sodium | 20 |
| Polyvinylpyrrolidone | 10 |
| Magnesium stearate | 5 |

The tablets may be prepared by conventional procedures well known in the pharmaceutical art and may be film coated with typical coating materials such as hydroxypropylmethylcellulose.

REFERENCES FOR STARTING MATERIALS

Ref1.: T. G. C. Bird and A. Olivier, Bioorg. Med. Chem. Lett., 6(5), 515–20, 1996.

Ref2.: M. J. Crimmin, P. R. Beckett and M. H. Davis, Patent WO 94/21625, 1994.

Ref3.: Prepared by treatment of commercially available 8-bromomethylquinoline with sodium iodide in acetone.

Ref4.: L. R. Hughes, A. L. Jackman, J. Oldfield, R. C. Smith, K. D. Burrows, P. R. Marsham, A. M. Bishiop, T. R. Jones, B. M. O'Conner and A. H. Calvert, J. Med. Chem., 33 (11), 3060, 1990.

Ref5.: M. R. Gowravaram, J. S. Johnson, D. Delecki, E. R. Cook, B. E. Tomczuk, A. K. Ghose, A. M. Mathiowetz, J. C. Spurlino, B. Rubin et al., J. Med. Chem., 38(14), 2570–81, 1995.

Ref6.: 7-Bromomethyl-1-methyl-2-oxo-1,2-dihydroquinoline was prepared by bromination of 1,7-dimethyl-2-quinolone [RN 67200-70-8; Imperial Chemical Industries PLC, ICI-Pharma S. A.; (Crawley, G. C., Hamon, A.) Eur. Pat. Appl., EP 385679 A2].

Ref7.: 5-Bromomethylquinoxaline—RN 131454-80-3; Kaken Pharmaceutical Co., Ltd.; (Maeda, T., Takae, M., Ishibashi, A., Ariyoshi, T., Yokoo, M.); Jpn. Kokai Tokkyo Koho, JP 02223558 A2.

Ref8.: 5-Bromomethyl-1-methyl-2-oxo-1,2-dihydroquinoline was prepared by bromination of 1,5-dimethyl-2-quinoline [RN 67200-69-5; Imperial Chemical Industries PLC, ICI-Pharma S. A.; (Crawley, G. C., Hamon, A.) Eur. Pat. Appl., EP 385679 A2].

Ref9.: 5-Bromomethyl-1-methyl-2,3-dioxoindoline—RN 139487-13-1; Imperial Chemical Industries PLC, ICI-Pharma S. A.; (Bruneau, P. A. R., Crawley, G. C., Oldham, K.) Eur. Pat. Appl., EP 462831 A2.

Ref10.: 6-Bromomethylquinoxaline—RN 53967-21-8; Kees, K. L., Caggiano, T. J., Steiner, K. E. Fitzgerald, J. J., Kates, M. J., Christos, T. E., Kulishoff, J. M., Moore, R. D., McCaleb, M. L.; J. Med. Chem., (1965), 38(4), 617.

Ref11.: 7-Bromomethyl-2,3-dihydro-4-methyl-3-oxo-1,4-benzoxazine—RN 139502-99-1; Imperial Chemical Industries PLC, ICI-Pharma S. A.: (Bruneau, P. A. R., Crawley, G. C.) Eur. Pat. Appl., EP 462813 A2.

Ref12.: 5-Bromomethyl-2-oxo-1,2-dihydroquinoline—RN 103702-28-9; Uchida, M., Tabusa, F., Komatsu, M., Morita, S., Kanbe, T., Nakagawa, K.; Chem. Pharm. Bull., (1985), 33 (9), 3775.

Ref13.: 5-Bromomethylbenzoxazole—RN 181038-98-2; Rhone Poulenc Rorer Ltd.; (Porter, B., Smith, C., Walsh, R. J. A., Majid, T. N., McCarthy, C., Harris, N. V., Astles, P. C., McLay, I. M., Morley, A. D., et al.) PCT Int. Appl., WO 9622978 A1.

Ref14.: 5-Bromomethyl-2-methylbenzothiazole—RN 125872-96-0; Toyama Chemical Co., Ltd.; (Hiraiwa, T., Takeda, K., Nakano, J., Sudani, M., Furuhata, K., Takata, M., Kawafuchi, H., Watanabe, I.) Ger. Offen., DE 3906920 A1.

What is claimed is:

1. A compound of the formula (I):

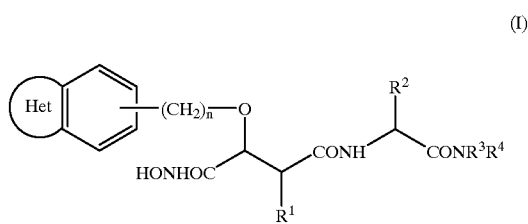

wherein:

n is 1 to 6;

Het is a nitrogen containing ring fused to the benzene ring on two adjacent carbon atoms to form a bicyclic ring system which ring system may be optionally substituted;

$R^1$ is hydrogen, $C_{1-8}$alkyl, $C_{2-6}$alkenyl, $C_{2-6}$alkynyl, $C_{3-8}$cycloalkyl, aryl, heteroaryl, heterocyclyl, aryl$C_{1-6}$alkyl, heteroaryl$C_{1-6}$alkyl, heterocyclyl$C_{1-6}$alkyl or $C_{3-8}$cycloalkyl$C_{1-6}$alkyl;

$R^2$ is $C_{1-6}$alkyl, $C_{2-6}$alkenyl, aryl$C_{1-6}$alkyl, heteroaryl$C_{1-6}$alkyl or the side-chain of a naturally occurring amino acid;

$R^3$ is hydrogen, $C_{1-6}$alkyl, $C_{3-8}$cycloalkyl, $C_{4-8}$cycloalkenyl, aryl$C_{1-6}$alkyl, heteroaryl$C_{1-6}$alkyl or heterocyclyl$C_{1-6}$alkyl;

$R^4$ is hydrogen or $C_{1-6}$alkyl; or $R^3$ and $R^4$ together with the nitrogen atom to which they are joined form a heterocyclic ring;

wherein any group or ring, in $R^1$–$R^4$, is optionally substituted;

or a pharmaceutically acceptable salt or in vivo hydroysable ester thereof.

2. A compound according to claim 1 wherein Het is a 5- or 6-membered ring containing one or two ring nitrogen atoms.

3. A compound according to claim 1 wherein Het and the benzene ring to which it is fused forms a quinoline, isoquinoline, quinazoline, 1-methyl-2-oxo-1,2-dihydroquinoline, 2-methyl-4-hydroxyquinazoline or 2-methyl-4-hydroxy-7-bromoquinazoline bicyclic ring system.

4. A compound according to claim 1 wherein Het and the benzene ring to which it is fused forms a benzoxazole or 2-methylbenzothiazole bicyclic ring system.

5. A compound of the formula (II):

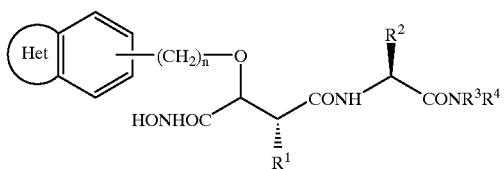

(II)

wherein n is 1; Het is of the sub-formula (ii) or (iii):

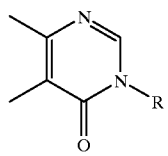

(ii)

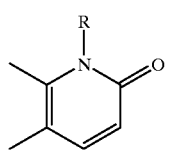

(iii)

wherein either of such rings is unsubstituted or substituted by one or two groups selected from halogen, $C_{1-6}$alkyl $C_{1-6}$alkoxy, $C_{1-6}$alkylamino or di-$C_{1-6}$alkylamino;
$R^1$ is isobutyl;
$R^2$ is isobutyl, tert-butyl or benzyl;
$R^3$ is methyl, ethyl, n-propyl, isobutyl, tert-butyl, 2-dimethylaminoethyl or benzyl; and
$R^4$ is hydrogen or methyl.

6. A compound according to claim 1 which is:
$N^2$-[4-(N-hydroxyamino)-2R-isobutyl-3S-(1'-methyl-2'-oxo-1',2'-dihydroquinolin-6'-yl)methoxysuccinyl]-L-tert-leucine-$N^1$-methylamide;
$N^2$-[4-(N-hydroxyamino)-2R-isobutyl-3S-(quinolin-8'-yl)methoxysuccinyl]-L-tert-leucine-$N^1$-methylamide;
$N^2$-[4-(N-hydroxyamino)-2R-isobutyl-3S-(2'-methyl-4'-oxo-3',4'-dihydroquinazolin-6'-yl)methoxysuccinyl]-L-tert-leucine-$N^1$-methylamide;
$N^2$-[4-(N-hydroxyamino)-2R-isobutyl-3S-(7'-bromo-2'-methyl-4'-oxo-3',4'-dihydroquinzolin-6'-yl) methoxysuccinyl]-L-tert-leucine-$N^1$-methylamide;
$N^2$-[4-(N-hydroxyamino)-2R-isobutyl-3S-(1'-methyl-2'-oxo-1',2'-dihydroquinolin-6'-yl)methoxysuccinyl]-L-tert-leucine-$N^1$-dimethylamide;
$N^2$-[4-(N-hydroxyamino)-2R-isobutyl-3S-(1'-methyl-2'-oxo-1',2'-dihydroquinolin-6'-yl)methoxysuccinyl]-L-tert-leucine-$N^1$-(2-dimethylaminoethyl)amide;
$N^2$-[4-(N-hydroxyamino)-2R-(4'-benzyloxy)butyl-3S-(1'-methyl-2'-oxo-1',2'-dihydroquinolin-6'-yl) methoxysuccinyl]-L-tert-leucine-$N^1$-methylamide;
$N^2$-[4-(N-hydroxyamino)-2R-isobutyl-3S-(quinolin-8'-yl)methoxysuccinyl]-L-tert-leucine-$N^1$-dimethylamide;
$N^2$-[4-(N-Hydroxyamino)-2R-isobutyl-3S-(quinolin-8'-yl)methoxysuccinyl]-L-tert-leucine-$N^1$-(2-dimethylaminoethyl)amide;
$N^2$-[4-(N-hydroxyamino)-2R-isobutyl-3S-(4'-oxo-3',4'-dihydroquinazolin-6'-yl)methoxysuccinyl]-L-tert-leucine-$N^1$-methylamide;

$N^2$-[4-(N-hydroxyamino)-2R-(4'-benzyloxy)butyl-3S-(quinolin-8'-yl)methoxysuccinyl]-L-tert-leucine-$N^1$-methylamide;
$N^2$-[4-(N-hydroxyamino)-2R-(3'-benzyloxy)propyl-3S-(2'-methyl-4'-oxo-3',4'-dihydroquinzolin-6'-yl) methoxysuccinyl]-L-tert-leucine-$N^1$-methylamide;
$N^2$-[4-(N-hydroxyamino)-2R-isobutyl-3S-(1'-methyl-2'-oxo-1',2'-dihydroquinolin-7'-yl)methoxysuccinyl]-L-tert-leucine-$N^1$-methylamide;
$N^2$-[4-(N-hydroxyamino)-2R-isobutyl-3S-(quinoxalin-5'-yl)methoxysuccinyl]-L-tert-leucine-$N^1$-methylamide;
$N^2$-[4-(N-hydroxyamino)-2R-isobutyl-3S-(1'-methyl-2'-oxo-1',2'-dihydroquinolin-5'-yl)methoxysuccinyl]-L-tert-leucine-$N^1$-methylamide;
$N^2$-[4-(N-hydroxyamino)-2R-isobutyl-3S-(1'-methyl-2',3'-dioxoindolin-5'-yl)methoxysuccinyl]-L-tert-leucine-$N^1$-methylamide;
$N^2$-[4-(N-hydroxyamino)-2R-isobutyl-3S-(1'-methyl-2'oxo-1',2',3',4'-tetrahydroquinolin-6'-yl) methoxysuccinyl]-L-tert-leucine-$N^1$-methylamide;
$N^2$-[4-(N-hydroxyamino)-2R-isobutyl-3S-(quinoxalin-6'-yl)methoxysuccinyl]-L-tert-leucine-$N^1$-methylamide;
$N^2$-[4-(N-hydroxyamino)-2R-isobutyl-3S-(2,3-dihydro-4-methyl-3-oxo-1,4-benzoxazin-7-yl) methoxysuccinyl]-L-tert-leucine-$N^1$-methylamide;
$N^2$-[4-(N-hydroxyamino)-2R-isobutyl-3S-(2'-oxo-1',2'-dihydroquinolin-5'-yl)methoxysuccinyl]-L-tert-leucine-$N^1$-methylamide;
$N^2$-[4-(N-hydroxyamino)-2R-isobutyl-3S-(benzoxazol-5'-yl)methoxysuccinyl]-L-tert-leucine-$N^1$-methylamide;
$N^2$-[4-(N-hydroxyamino)-2R-isobutyl-3S-(2'methylbenzothiazol-5'-yl)methoxysuccinyl]-L-tert-leucine-$N^1$-methylamide;

or a pharmaceutically acceptable salt.

7. A pharmaceutical composition which comprises a compound according to any one of claims 1–4, 6 and 5 and a pharmaceutically acceptable carrier.

8. A process for preparing a compound according to any one of claims 1–4, 6 and 5 or a pharmaceutically acceptable salt or in vivo hydrolysable ester thereof which process comprises a) reacting a compound of the formula (III):

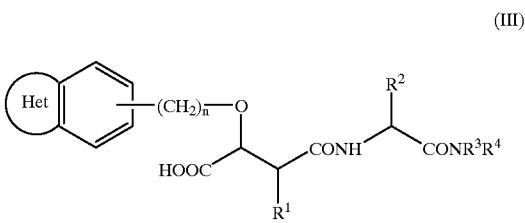

(III)

wherein n, Het and $R^1$–$R^4$ are as defined in claim 1, or an activated derivative thereof with hydroxylamide, O-protected hydroxylamine or a salt thereof; or b) coupling a compound of the formula (IV) with a compound of the formula (V):

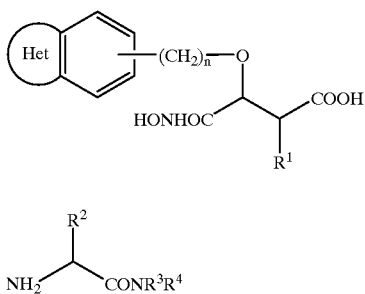

(IV)

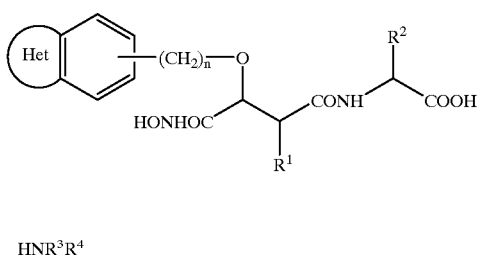

(V)

wherein n, Het and $R^1$–$R^4$ are as defined in claim 1, under standard peptide coupling conditions; or c) reacting a compound of the formula (VI) with compound of the formula (VII):

(VI)

HNR³R⁴ (VII)

wherein n, Het and R–$R^4$ are as defined in claim 1:
wherein any functional group is protected, if necessary, and:
  i. removing any protecting groups;
  ii. optionally forming a pharmaceutically acceptable salt or in vivo hydrolysable ester.

9. A compound of the formula (III):

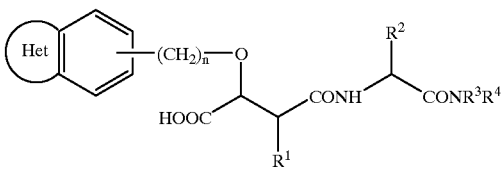

(III)

wherein:

n is 1 to 6;

Het is a nitrogen containing ring fused to the benzene ring on two adjacent carbon atoms to form a bicyclic ring system which ring system may be optionally substituted;

$R^1$ is hydrogen, $C_{1-8}$alkyl, $C_{2-6}$alkenyl, $C_{2-6}$alkynyl, $C_{3-8}$cycloalkyl, aryl, heteroaryl, heterocyclyl, aryl$C_{1-6}$alkyl, heteroaryl$C_{1-6}$alkyl, heterocyclyl$C_{1-6}$alkyl or $C_{3-8}$cycloalkyl$C_{1-6}$alkyl;

$R^2$ is $C_{1-6}$alkyl, $C_{2-6}$alkenyl, aryl$C_{1-6}$alkyl, heteroaryl$C_{1-6}$alkyl or the side-chain of a naturally occurring amino acid;

$R^3$ is hydrogen, $C_{1-6}$alkyl, $C_{3-8}$-cycloalkyl, $C_{4-8}$cycloalkenyl, aryl$C_{1-6}$alkyl, heteroaryl$C_{1-6}$alkyl or heterocycyl$C_{1-6}$alkyl;

$R^4$ is hydrogen or $C_{1-6}$alkyl; or $R^3$ and $R^4$ together with the nitrogen atom to which they are joined form a heterocyclic ring;

wherein any group or ring, in $R^1$–$R^4$, optionally substituted.

* * * * *